US010188739B2

(12) United States Patent
Jain et al.

(10) Patent No.: US 10,188,739 B2
(45) Date of Patent: Jan. 29, 2019

(54) COMPOSITIONS AND METHODS FOR ADMINISTERING INSULIN OR INSULIN-LIKE PROTEIN TO THE BRAIN

(71) Applicant: Xenetic Biosciences, Inc., Lexington, MA (US)

(72) Inventors: Sanjay Jain, London (GB); Dmitry Genkin, Saint Petersburg (RU); Henry Hoppe, Moultonborough, NH (US)

(73) Assignee: XENETIC BIOSCIENCES, INC., Lexington, MA (US)

(*) Notice: Subject to any disclaimer, the term of this patent is extended or adjusted under 35 U.S.C. 154(b) by 0 days.

(21) Appl. No.: 14/632,967

(22) Filed: Feb. 26, 2015

(65) Prior Publication Data

US 2015/0238620 A1 Aug. 27, 2015

Related U.S. Application Data

(60) Provisional application No. 61/945,423, filed on Feb. 27, 2014.

(51) Int. Cl.
*A61K 38/28* (2006.01)
*A61K 47/48* (2006.01)
*A61K 47/61* (2017.01)
*A61K 9/00* (2006.01)

(52) U.S. Cl.
CPC .......... *A61K 47/4823* (2013.01); *A61K 38/28* (2013.01); *A61K 47/61* (2017.08); *A61K 9/0043* (2013.01); *Y02A 50/473* (2018.01)

(58) Field of Classification Search
CPC ... A61K 38/28; A61K 47/4823; A61K 9/0043
See application file for complete search history.

(56) References Cited

U.S. PATENT DOCUMENTS

| | | | |
|---|---|---|---|
| 5,679,645 A | 10/1997 | Ikeuichi et al. |
| 5,824,784 A | 10/1998 | Kinstler et al. |
| 5,846,951 A | 12/1998 | Gregoriadis |
| 6,323,311 B1 | 11/2001 | Liu et al. |
| 6,956,027 B2 | 10/2005 | Kinstler |
| 6,962,972 B2 | 11/2005 | Gregoriadis |
| 7,128,913 B2 | 10/2006 | Burg et al. |
| 7,074,755 B2 | 11/2006 | Heavner |
| 7,807,824 B2 | 10/2010 | Jain et al. |
| 7,875,708 B2 | 1/2011 | Jain et al. |
| 2004/0082765 A1 | 4/2004 | Nakamura et al. |
| 2007/0014759 A1 | 1/2007 | DeFrees et al. |
| 2007/0083006 A1 | 4/2007 | Hinds et al. |
| 2007/0191597 A1 | 8/2007 | Jain et al. |
| 2010/0022441 A1 | 1/2010 | Jain et al. |

FOREIGN PATENT DOCUMENTS

| | | |
|---|---|---|
| CA | 1156217 A | 11/1983 |
| EP | 550108 A1 | 7/1993 |
| EP | 1219636 A2 | 7/2003 |
| EP | 1681303 A1 | 7/2006 |
| RU | 2141531 C1 | 11/1999 |
| WO | 9105867 A1 | 5/1991 |
| WO | 9222331 A1 | 12/1992 |
| WO | 9943307 A1 | 9/1999 |
| WO | 200187272 A2 | 11/2001 |
| WO | 200187922 A2 | 11/2001 |
| WO | 2003031464 A2 | 4/2003 |
| WO | 2003055526 A2 | 7/2003 |
| WO | 2004091494 A2 | 10/2004 |
| WO | 2004101619 A1 | 11/2004 |
| WO | 2005003149 A1 | 1/2005 |
| WO | 2005014050 A2 | 2/2005 |
| WO | 2005016973 A1 | 2/2005 |
| WO | 2005016974 A1 | 2/2005 |
| WO | 2005037320 A2 | 4/2005 |
| WO | 2005055946 A2 | 6/2005 |
| WO | 2006000540 A1 | 1/2006 |
| WO | 2005016161 A1 | 2/2006 |
| WO | 2006016168 A2 | 2/2006 |
| WO | 2006074467 A2 | 7/2006 |
| WO | 2006082184 A2 | 8/2006 |
| WO | 2006090119 A1 | 8/2006 |
| WO | 2007047922 A2 | 4/2007 |
| WO | 2008012528 A1 | 1/2008 |
| WO | 2008012540 A1 | 1/2008 |

OTHER PUBLICATIONS

Ott et al., Diab. Obesity and Metab. 14: 214-221, 2012.*
Chao et al., JBC 274:18206-18212, 1999.*
Banks et al., Pharmacol Ther., 136(1): 82-93, 2012.*
Almeida et al., "Solid lipid nanoparticles as a drug delivery system for peptides and proteins." Advance Drug Delivery Reviews, 2007 (59):478-490.
Brownlee et al., "A glucose controlled insulin delivery system semi synthetic insulin bound to Lectin," Science v. 206, No. 4423, 1979, pp. 1190-1191.
Caliceti, et al., S.T.P. Pharma Sciences (1999) 9(1):107-113.
Cuatrecasas, "Interaction of Insulin with the Cell Membrane: The Primary Action of Insulin." PNAS, v. 63, No. 2, Jun. 1969.
DeFrees, et al., "GlycoPEGylation of recombinant therapeutic proteins produced in *Escherichia coli*." Glycobiology, Sep. 2006;16(9):833-43. Epub May 22, 2006.
Ehrat et al., Biopolymers (1984) 22:569-573.
European Search Report EP 13 15 3525, dated Oct. 16, 2013.
Fan et al., "Preclinical evaluation of Hematide, a novel erythropoiesis stimulating agent, for the treatment of anemia." Exp Hematol. Oct. 2006;34(10):1303-11.

(Continued)

*Primary Examiner* — Gyan Chandra
(74) *Attorney, Agent, or Firm* — Entralta P.C.; James W. Collett; Peter D. Weinstein

(57) ABSTRACT

The present invention provides a method of intranasal delivery of a pharmaceutical composition, comprising a polysaccharide derivative of insulin protein and a one or more pharmaceutically acceptable excipients, to a subject, wherein the insulin protein is delivered to the brain of the subject through the nasal mucosa.

19 Claims, 4 Drawing Sheets

Specification includes a Sequence Listing.

(56) References Cited

OTHER PUBLICATIONS

Fernandes et al., Biochimica et Biophysica Acta (1996) 1293:90-96.
Fernandes et al., Biochimica et Biophysica Acta (1997) 1341:26-34.
Geiger et al., "Insulin: Chemistry, Structure, and Function of Insulin and Related Hormones." Branderburg and Wollmer, (eds.)Walter de Gruyter & Co., New York (1980) pp. 409-415.
Gregoriadis et al., "Improving the therapeutic efficacy of peptides and proteins: A role for polysialic acids." International Journal of Pharmaceutics, v. 300, No. 1-2, pp. 125-130, Aug. 26, 2005.
Gregoriadis et al., FEBS Letters (1993) 315: 271-276.
Hinds et al., Advanced Drug Delivery Reviews (2002)54:505-530.
Hinds et al., bioconjugate Chemistry (2000) 11:195-201 (Abstract only).
International Search Report PCT/GB2007/002821, dated Dec. 21, 2007.
Jain et al. "Polysialylated insulin: synthesis, characterization and biological activity in vivo." BBA—General Subjects v. 1622, No. 1, pp. 42-49, Jun. 20, 2003.
Jain et al., "Polysialylation: the natural way to improve the stabililty and pharmacokinetics of protein and peptide drugs." Drug Delivery Systems and Science, 2004, 4(1):3-9.
Kinstler et al., "Mono-N-termininal poly(ehtylene glycol)-protein conjugates." Advance Drug Delivery Reviews, 2002 54 (4):477-485.
Krystal, "A simple microassay for erythropoietin based on H-thymidine incorporation into spleen cells prom phylhydrazine treated mice." 1983 11(7):649-660.
Lifely et al., "Sialic Acid Polysaccharide Antigens of Neisseria meingitis and *Escherichia coli*; Esterification Between Adjacent Residues." 1981 (94):193-203.
Molineux, et al., "The design and development of pegfilgrasim (PEG-rhetHuG-CSF, Neulasta)." Curr. Pharm Des. 2004;10(11):1235-44.
Park et al., Journal of Biological Chemistry (1949) 181:149-151.
Sato et al., "Glycoinsulins: Dendritic Sialyloligosaccharide-Displaying Insulins Showing a Prolonged Blood-Sugar-Lowering Activity." J. of American Chemical Society, v. 126, No. 43, pp. 14013-14022, Nov. 11, 2004.
Sato et al., Abgew Chew Int Ed., 43:1516-1520, Dec. 31, 2004.
Shafer et al. "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides." 2000 Vaccines 18:1273-1281.
Sinicropi et al., "Colorimetric Determination of Dnase I Activity with DNA-Methyl Green Substrate." 1994 (222):351-358.
Svennerholm, biochimica et Biophysica Acta (1957) 24:604-611.
Uchio et al., Advanced Drug Delivery Reviews (1999) 35:289-306.
Wang, International Journal of Pharmaceutics (1999) 185:129-188.
Written Opinion of the International Search Authority PCT/GB2007/002821, dated Jan. 25, 2009.
Zhang et al. "Obestatis, a peptide encoded by the ghrelin gene, opposes gherlin's effects on food intake," Science, Nov. 11, 2005; 310(5750):996-999. (Abstract only).

* cited by examiner

COMPOSITIONS AND METHODS FOR ADMINISTERING INSULIN OR INSULIN-LIKE PROTEIN TO THE BRAIN

This is a continuation that claims priority under 35 U.S.C. § 119(e) to U.S. Provisional Patent Application 61/945,423 filed on Feb. 27, 2014, the entire contents of which is hereby incorporated by reference.

Insulin is a naturally-occurring polypeptide hormone secreted by the pancreas and required by the cells of the body to remove and use glucose from the blood. Insulin tightly regulates glucose uptake and metabolism, and therefore modulation of insulin activity and in turn glucose levels in the blood can have significant physiological effects. Many pathologies are either caused or enhanced by variations in insulin levels and the onset of insulin tolerance or resistance (i.e. a state where cells become less responsive or unresponsive to the insulin signal). The biological role for insulin action in energy homeostasis and appetite regulation and diabetes mellitus is well established.

Insulin resistance has been associated with various diseases and disorders, including but not limited to, e.g., type-2 diabetes, obesity, systemic inflammation, chronic pancreatitis, hypertension, hyperglycycemia, dyslipidemia, promoting weight loss, gestational diabetes, colon cancer, prostate cancer, pancreatic cancer, chronic liver disease, neurogenerative disorders, e.g., Alzheimers disease, and hepatitis C virus (HCV) infection in a mammalian subject.

Insulin has been shown to play a role in the function of the central nervous system, having significant impact within the brain, functioning as a key neuromodulator in behavioral, cellular, biochemical and molecular studies. The brain is now regarded as an insulin-sensitive organ with widespread, yet selective, expression of the insulin receptor in the olfactory bulb, hypothalamus, hippocampus, cerebellum, amygdala and cerebral cortex. Insulin receptor signaling in the brain is important for neuronal development, glucoregulation, feeding behavior, body weight, and cognitive processes such as with attention, executive functioning, learning and memory. Emerging evidence has demonstrated insulin receptor signaling to be impaired in several neurological disorders. Moreover, insulin receptor signaling is recognized as important for dendritic outgrowth, neuronal survival, circuit development, synaptic plasticity and post-synaptic neurotransmitter receptor trafficking.

Insulin has various memory-related physiological and pharmacological actions. For instance, insulin increases the uptake and metabolism of glucose by brain cells, thus enhancing the oxidative metabolism and ATP production by neurons. Augmenting the oxidative phosphorylation inside neurons prevents abnormally high intraneuronal acidosis; increased acidosis is known to enhance the formation of β-Amyloid (Aβ) inside neurons. In addition, insulin seems to modulate long-term potentiation through influencing brain cell expression of NMDA receptors. Insulin also increases the levels of some CNS neurotransmitters such as acetylcholine and norepinephrine which modulate the cerebral blood flow and cognitive power of the brain. Furthermore, insulin increases the level of Insulin degrading enzyme (IDE) in brain tissues. IDE is a $Zn^{2+}$ metalloprotease that degrades Aβ and plays a crucial role in its clearance in the brain.

Over the years, there have been extensive research and development efforts devoted to identifying and commercializing insulin-based compositions and therapies to address these various disorders. And while there has been significant advancements made to date, there still exists a need for improved compositions and methods to more effectively address these disorders.

Insulin is most commonly administered by subcutaneous injection, typically into the abdomen or upper thighs. In order to maintain acceptable blood glucose levels, it is often necessary to inject insulin at least once or twice per day, with supplemental injections of rapid-acting insulin being administered when necessary. Aggressive treatment of diabetes can require even more frequent injections, where the patient closely monitors blood glucose levels using home diagnostic kits.

The administration of insulin by injection is undesirable in a number of respects. First, many patients find it difficult and burdensome to inject themselves as frequently as necessary to maintain acceptable blood glucose levels. Such reluctance can lead to non-compliance, which in the most serious cases can be life-threatening. Moreover, systemic absorption of insulin from subcutaneous injection is relatively slow, frequently requiring from 45 to 90 minutes, even when fast-acting insulin formulations are employed. Thus, it has long been a goal to provide alternative insulin formulations and routes of administration which avoid the need for self-injection and which can provide rapid systemic availability of the insulin The intranasal route has been explored as a non-invasive method to circumvent the blood-brain barrier for transport of drugs to the central nervous system (CNS). The intranasal route of administration allows the pharmaceutical composition to travel through the roof of the nose. The pharmaceutical compositions travel from the roof of the nose along the fibers of the olfactory and trigeminal nerves (Cranial Nerves I & V), found in the mucosa of the nose, to the extracellular space of the neurons of the brain and spinal cord. As such, the rest of the body's organs are not exposed to the drug, reducing its side effects and required dosage. Although intranasal delivery to the CNS has been demonstrated for a number of small molecules and some peptides and smaller proteins, there is little evidence demonstrating the delivery of protein macromolecules to the CNS via intranasal pathways, presumably due to the larger size and varying physico-chemical properties unique to each macromolecule or class of macromolecules, that may hinder direct nose-to-brain delivery.

Intranasal delivery of insulin has emerged as a potentially effective means of introducing this hormone to the brain without a significant rise in its circulating levels (Hanson and Frey, BMC Neuroscience 9 (suppl 3):S5 (2008)).

REFERENCE TO A SEQUENCE LISTING

Sequence Listing file Name: 2015_02_26_Sequence_Listing_3 IPXN1_0034 US_ST25.txt
Sequence Listing file Size: 4 kb
The entire contents of the sequence listing are hereby expressly incorporated by reference.

SUMMARY

Aspects of the present specification disclose a method of delivery of a therapeutically effective amount of a protein to the brain of an individual. A method disclosed herein comprises intranasal administration of a pharmaceutical composition comprising a population of the protein attached with a polysaccharide. The protein may be an insulin or insulin-like protein and the polysaccharide may be an anionic polysaccharide like polysialic acid.

Other aspects of the present specification disclose a method of treating a neurological disorder. A method disclosed herein comprises administering to the brain of the individual a pharmaceutical composition comprising a population of a protein attached with a polysaccharide as disclosed herein. A pharmaceutical composition disclosed herein may be administered intranasally and the protein delivered to the brain through the nasal mucosa. The neurological disorder may be a memory disorder, a head injury, a spinal cord injury, a seizure, a stroke, a dementia, a memory loss, an attention deficit disorder (ADD), an epilepsy, an ischemia, a Amyotrophic Lateral Sclerosis (ALS), a multiple sclerosis, a Huntington's disease, a Parkinson's disease, a Alzheimer's disease, CNS damage resulting from infectious disease, CNS damage resulting from a tumor, a mood disorder, an anxiety disorder, a memory disorder, or a schizophrenic disorder.

Other aspects of the present specification disclose a method of treating insulin resistance in an individual. A method disclosed herein comprises administering to the brain of the individual a pharmaceutical composition comprising a population of a protein attached with a polysaccharide as disclosed herein. A pharmaceutical composition disclosed herein may be administered intranasally and the protein delivered to the brain through the nasal mucosa. The insulin resistance may be associated with type-2 diabetes, obesity, systemic inflammation, chronic pancreatitis, hypertension, hyperglycyemia, dyslipidemia, promoting weight loss, gestational diabetes, colon cancer, prostate cancer, pancreatic cancer, or chronic liver disease.

Other aspects of the present specification disclose a use of a pharmaceutical composition disclosed herein in the manufacture of a medicament for the treatment of a neurological disorder or insulin resistance.

Other aspects of the present specification disclose a use of a pharmaceutical composition disclosed herein in treating a neurological disorder or insulin resistance.

Other aspects of the present specification disclose a use of a pharmaceutical composition disclosed herein in the manufacture of a medicament for the administration of a therapeutically effective amount of the protein to the brain of an individual.

Other aspects of the present specification disclose a use of a pharmaceutical composition disclosed herein in administering a therapeutically effective amount of the protein to the brain of an individual.

DETAILED DESCRIPTION

Figure 1:
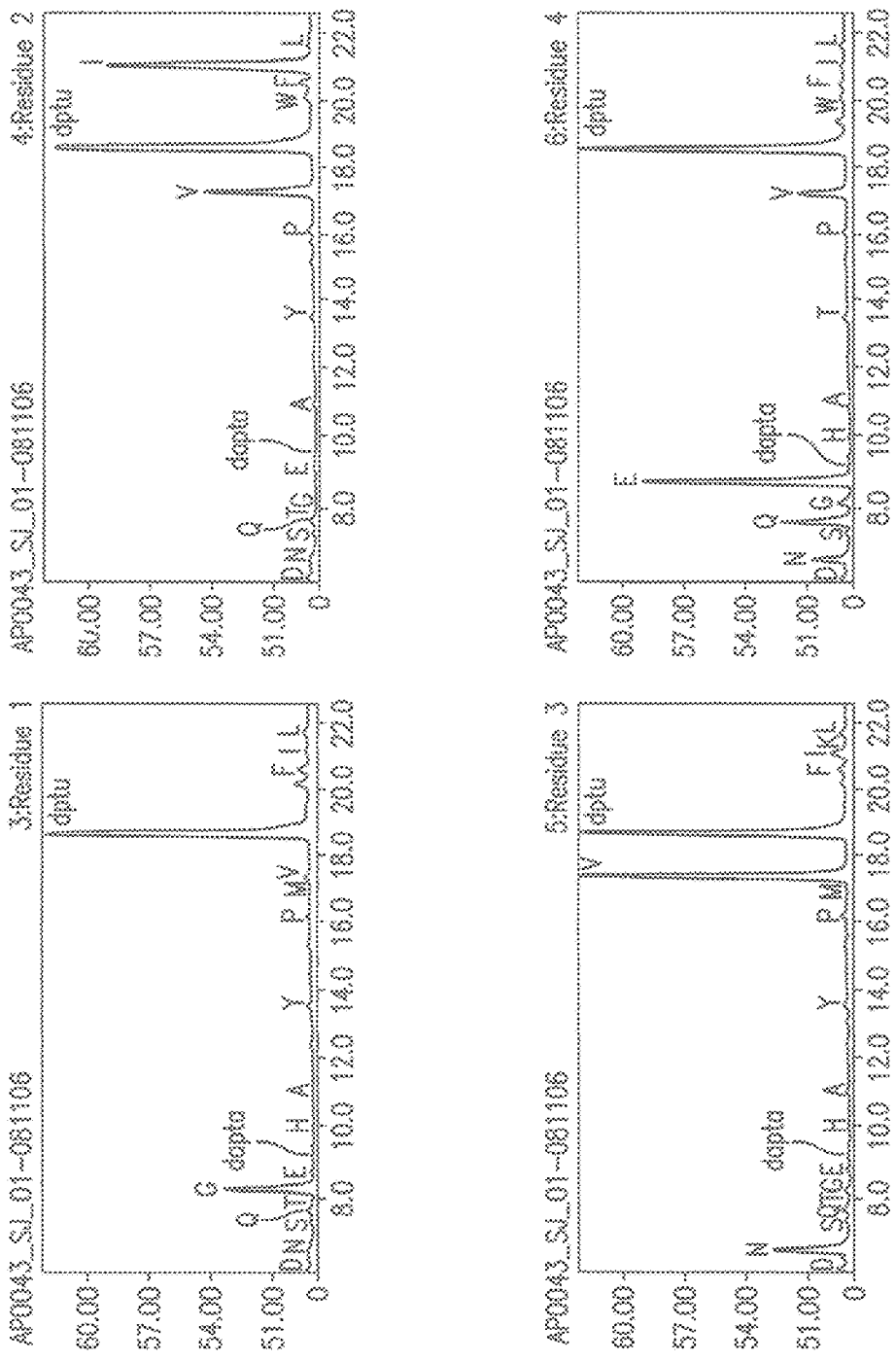
FIG. 1 shows Edman amino acid degradation results.

Aspects of the present specification disclose a composition comprising a population of polysaccharide derivatives of a protein. By "population" we mean that there is more than one protein attached with a polysaccharide disclosed herein (i.e., a polysaccharide derivative) in the composition. In aspects, a population may comprise, e.g., 1,000 or more proteins attached with a polysaccharide disclosed herein, 10,000 or more proteins attached with a polysaccharide disclosed herein, 50,000 or more proteins attached with a polysaccharide disclosed herein, 75,000 or more proteins attached with a polysaccharide disclosed herein, 100,000 or more proteins attached with a polysaccharide disclosed herein, 250,000 or more proteins attached with a polysaccharide disclosed herein, 500,000 or more proteins attached with a polysaccharide disclosed herein, 750,000 or more proteins attached with a polysaccharide disclosed herein, or 1,000,000 or more proteins attached with a polysaccharide disclosed herein.

A population of proteins attached with a polysaccharide disclosed herein has a narrow polydispersity range. In aspects of this embodiment, a population of proteins attached with a polysaccharide disclosed herein has a polydispersity of, e.g., less than 1.3, less than 1.25, less than 1.2, less than 1.15, less than 1.1, or less than 1.05. In other aspects of this embodiment, a population of proteins attached with a polysaccharide disclosed herein has a polydispersity range of, e.g., about 1.05 to about 1.3, about 1.05 to about 1.25, about 1.05 to about 1.2, about 1.05 to about 1.15, about 1.05 to about 1.1, about 1.1 to about 1.3, about 1.1 to about 1.25, about 1.1 to about 1.2, about 1.1 to about 1.15, about 1.15 to about 1.3, about 1.15 to about 1.25, or about 1.15 to about 1.2.

In an embodiment, the population consists substantially only of proteins having a polysaccharide disclosed herein attached to the N-terminus of the protein (i.e., an N-terminal derivatives of a protein). The degree of derivatisation at the N-terminus may be determined using standard techniques in the art, such as peptide mapping or Edman Degradation. In aspects of this embodiment, a population of N-terminal derivatives of a protein has, e.g., about 70%, about 75%, about 80%, about 85%, about 90% or about 95% of the proteins derivatized at the N-terminus with a polysaccharide disclosed herein. In other aspects of this embodiment, a population of N-terminal derivatives of a protein has, e.g., at least 70%, at least 75%, at least 80%, at least 85%, at least 90% or at least 95% of the proteins derivatized at the N-terminus with a polysaccharide disclosed herein. In yet other aspects of this embodiment, a population of N-terminal derivatives of a protein has, e.g., at most 70%, at most 75%, at most 80%, at most 85%, at most 90% or at most 95% of the proteins derivatized at the N-terminus with a polysaccharide disclosed herein.

In still other aspects of this embodiment, a population of N-terminal derivatives of a protein has between, e.g., about 70% to about 75%, about 70% to about 80%, about 70% to about 85%, about 70% to about 90%, about 70% to about 95%, about 70% to about 96%, about 70% to about 97%, about 70% to about 98%, about 70% to about 99%, about 70% to about 100%, about 75% to about 80%, about 75% to about 85%, about 75% to about 90%, about 75% to about 95%, about 75% to about 96%, about 75% to about 97%, about 75% to about 98%, about 75% to about 99%, about 75% to about 100%, about 80% to about 85%, about 80% to about 90%, about 80% to about 95%, about 80% to about 96%, about 80% to about 97%, about 80% to about 98%, about 80% to about 99%, about 80% to about 100%, about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, or about 95% to about 100% of the proteins derivatized at the N-terminus with a polysaccharide disclosed herein.

In another aspect of this embodiment, a composition comprises a population of polysaccharide derivatives of an insulin wherein the polysaccharide is anionic and comprises between 2 and 200 saccharide units, and wherein the population consists substantially only of N-terminal derivatives of the insulin. In another aspect of this embodiment, a composition comprises a population of polysaccharide derivatives of insulin wherein the polysaccharide is anionic and comprises between 2 and 125 saccharide units, and wherein the population consists substantially only of N-terminal derivatives of the insulin. In another aspect of this embodiment, a composition comprises a population of polysaccharide derivatives of insulin wherein the polysaccharide is anionic and comprises between 2 and 80 saccharide units, and wherein the population consists substantially only of N-terminal derivatives of the insulin. In another aspect of this embodiment, a composition comprises a population of polysaccharide derivatives of insulin wherein the polysaccharide is anionic and comprises between 5 and 80 saccharide units, and wherein the population consists substantially only of N-terminal derivatives of the insulin. In another aspect of this embodiment, a composition comprises a population of polysaccharide derivatives of insulin wherein the polysaccharide is anionic and comprises between 10 and 80 saccharide units, and wherein the population consists substantially only of N-terminal derivatives of the insulin.

In certain embodiments, the polysaccharide may be a naturally occurring polysaccharide, or a derivative of a naturally occurring polysaccharide, for instance, a polysaccharide which has been derivatized by a reaction of one or more active groups on the saccharide residues, or which has been covalently linked to a derivatising group at the end of the polysaccharide chain. A polysaccharide may be an anionic polysaccharide. An anionic polysaccharide disclosed herein includes, without limitation, polysialic acid, heparin, hyaluronic acid and chondroitin sulphate.

In an embodiment, an anionic polysaccharide is a polysialic acid (PSA). Polysialic acids (PSAs) are naturally occurring unbranched polymers of sialic acid produced by certain bacterial strains and in mammals in certain cells. They can be produced in various degrees of polymerisation from n=about 200 or more sialic acid residues down to n=2 by limited acid hydrolysis or by digestion with neuraminidases, or by fractionation of the natural, bacterially derived forms of the polymer.

In certain embodiments, the polysialic acid is derived from a bacterial source, for instance polysaccharide B of *E. coli* KI, *N. meningitidis*, *Maraxella liquefaciens* or *Pasteurella aeruginosa* or K92 polysaccharide from *E. coli* K92 strain. In an embodiment, the alpha-2,8-linked PSA of *E. coli* strain K1 (also known as 'colominic acid' (CA)) and is used (in various lengths).

The composition of different PSAs also vary such that: 1) there are homopolymeric forms, i.e., the alpha-2,8-linked PSA comprising the capsular polysaccharide of *E. coli* strain K1 and of the group-B *meningococci*, which is also found on the embryonic form of the neuronal cell adhesion molecule (N-CAM); 2) there are heteropolymeric forms, such as the alternating alpha-2,8 alpha-2,9 PSA of *E. coli* strain K92 and the group C polysaccharides of *N. meningitides*; and 3) there are alternating copolymers containing sialic acids monomers other than sialic acid such as group W135 or group Y of *N. meningitidis*. PSAs have important biological functions including the evasion of the immune and complement systems by pathogenic bacteria and the regulation of glial adhesiveness of immature neurons during foetal development (wherein the polymer has an anti-adhesive function). There are no known receptors for PSAs in mammals.

In recent years, the biological properties of polysialic acids, particularly those of the alpha-2,8 linked homopolymeric polysialic acid have been exploited to modify the pharmacokinetic properties of protein and low molecular weight drug molecules. Polysialic acid derivatisation gives rise to dramatic improvements in circulating half-life for a number of therapeutic proteins including catalase and asparaginase, and also allows such proteins to be used in the face of pre-existing antibodies raised as an undesirable (and sometimes inevitable) consequence of prior exposure to the therapeutic protein. The alpha-2,8 linked polysialic acid offers an attractive alternative to PEG, being an immunologically invisible biodegradable polymer which is naturally part of the human body, and which degrades, via tissue neuraminidases, to sialic acid, a non-toxic saccharide.

In aspects of this embodiment, a polysaccharide disclosed herein consists substantially only of sialic acid units. In other aspects of this embodiment, a polysaccharide disclosed herein may have units other than sialic acid in the molecule, e.g., sialic acid units may alternate with other saccharide units.

In an embodiment, the polysaccharide disclosed herein may comprise the same or different numbers of saccharide units. In aspects of this embodiment, a polysaccharide disclosed herein attached to a protein comprises saccharide units of, e.g., about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 150, about 175, or about 200. In other aspects of this embodiment, polysaccharide disclosed herein attached to a protein comprises saccharide units of, e.g., at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 150, at least 175, or at least 200. In yet other aspects of this embodiment, a polysaccharide disclosed herein attached to a protein comprises saccharide units of, e.g., at most 2, at most 3, at most 4, at most 5, at most 6, at most 7, at most 8, at most 9, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95, at most 100, at most 105, at most 110, at most 115, at most 120, at most 125, at most 150, at most 175, or at most 200.

In still other aspects of this embodiment, a polysaccharide disclosed herein attached to a protein comprises saccharide units in the range of, e.g., about 2 to about 200, about 2 to about 175, about 2 to about 150, about 2 to about 125, about 2 to about 100, about 2 to about 90, about 2 to about 80, about 2 to about 75, about 2 to about 70, about 2 to about 60, about 2 to about 50, about 2 to about 40, about 2 to about 30, about 2 to about 25, about 2 to about 20, about 2 to about 15, about 2 to about 10, about 5 to about 200, about 5 to about 175, about 5 to about 150, about 5 to about 125, about 5 to about 100, about 5 to about 90, about 5 to about 80, about 5 to about 75, about 5 to about 70, about 5 to about 60, about 5 to about 50, about 5 to about 40, about 5 to about 30, about 5 to about 25, about 5 to about 20, about 5 to about 15, about 5 to about 10, about 10 to about 200, about 10 to about 175, about 10 to about 150, about 10 to about 125, about 10 to about 100, about 10 to about 90, about 10 to about 80, about 10 to about 75, about 10 to about 70, about 10 to about 60, about 10 to about 50, about 10 to about 40, about 10 to about 30, about 10 to about 25, about 10 to about 20, about 10 to about 15, about 20 to about 200, about 20 to about 175, about 20 to about 150, about 20 to about 100, about 20 to about 90, about 20 to about 80, about 20 to about 75, about 20 to about 70, about 20 to about 60, about 20 to about 50, about 20 to about 40, about 20 to about 30, about 30 to about 200, about 30 to about 175, about 30 to about 150, about 30 to about 100, about 30 to about 90, about 30 to about 80, about 30 to about 75, about 30 to about 70, about 30 to about 60, about 30 to about 50, about 30 to about 40, about 40 to about 200, about 40 to about 175, about 40 to about 150, about 40 to about 100, about 40 to about 90, about 40 to about 80, about 40 to about 75, about 40 to about 70, about 40 to about 60, about 40 to about 50, about 50 to about 200, about 50 to about 175, about 50 to about 150, about 50 to about 100, about 50 to about 90, about 50 to about 80, about 50 to about 75, about 50 to about 70, about 50 to about 60, about 60 to about 200, about 60 to about 175, about 60 to about 150, about 60 to about 100, about 60 to about 90, about 60 to about 80, about 60 to about 75, about 60 to about 70, about 70 to about 200, about 70 to about 175, about 70 to about 150, about 70 to about 100, about 70 to about 90, about 70 to about 80, about 70 to about 75, about 75 to about 200, about 75 to about 175, about 75 to about 150, about 75 to about 100, about 75 to about 90, about 75 to about 80, about 80 to about 200, about 80 to about 175, about 80 to about 150, about 80 to about 100, about 80 to about 90, about 90 to about 200, about 90 to about 175, about 90 to about 150, about 90 to about 100, about 100 to about 200, about 100 to about 175, about 100 to about 150, about 125 to about 200, about 125 to about 175, about 125 to about 150, about 150 to about 200, about 150 to about 175, or about 175 to about 200.

In aspects of this embodiment, a polysaccharide attached to a protein is a polysialic acid disclosed herein comprising sialic acid units of, e.g., about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 150, about 175, or about 200. In other aspects of this embodiment, a polysaccharide attached to a protein is a polysialic acid disclosed herein comprising sialic acid units of, e.g., at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 150, at least 175, or at least 200. In yet other aspects of this embodiment, a polysaccharide attached to a protein is a polysialic acid disclosed herein comprising sialic acid units of, e.g., at most 2, at most 3, at most 4, at most 5, at most 6, at most 7, at most 8, at most 9, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95, at most 100, at most 105, at most 110, at most 115, at most 120, at most 125, at most 150, at most 175, or at most 200.

In still other aspects of this embodiment, a polysaccharide attached to a protein is a polysialic acid disclosed herein comprising sialic acid units in the range of, e.g., about 2 to about 200, about 2 to about 175, about 2 to about 150, about 2 to about 125, about 2 to about 100, about 2 to about 90, about 2 to about 80, about 2 to about 75, about 2 to about 70, about 2 to about 60, about 2 to about 50, about 2 to about 40, about 2 to about 30, about 2 to about 25, about 2 to about 20, about 2 to about 15, about 2 to about 10, about 5 to about 200, about 5 to about 175, about 5 to about 150, about 5 to about 125, about 5 to about 100, about 5 to about 90, about 5 to about 80, about 5 to about 75, about 5 to about 70, about 5 to about 60, about 5 to about 50, about 5 to about 40, about 5 to about 30, about 5 to about 25, about 5 to about 20, about 5 to about 15, about 5 to about 10, about 10 to about 200, about 10 to about 175, about 10 to about 150, about 10 to about 125, about 10 to about 100, about 10 to about 90, about 10 to about 80, about 10 to about 75, about 10 to about 70, about 10 to about 60, about 10 to about 50, about 10 to about 40, about 10 to about 30, about 10 to about 25, about 10 to about 20, about 10 to about 15, about 20 to about 200, about 20 to about 175, about 20 to about 150, about 20 to about 100, about 20 to about 90, about 20 to about 80, about 20 to about 75, about 20 to about 70, about 20 to about 60, about 20 to about 50, about 20 to about 40, about 20 to about 30, about 30 to about 200, about 30 to about 175, about 30 to about 150, about 30 to about 100, about 30 to about 90, about 30 to about 80, about 30 to about 75, about 30 to about 70, about 30 to about 60, about 30 to about 50, about 30 to about 40, about 40 to about 200, about 40 to about 175, about 40 to about 150, about 40 to about 100, about 40 to about 90, about 40 to about 80, about 40 to about 75, about 40 to about 70, about 40 to about 60, about 40 to about 50, about 50 to about 200, about 50 to about 175, about 50 to about 150, about 50 to about 100, about 50 to about 90, about 50 to about 80, about 50 to about 75, about 50 to about 70, about 50 to about 60, about 60 to about 200, about 60 to about 175, about 60 to about 150, about 60 to about 100, about 60 to about 90, about 60 to about 80, about 60 to about 75, about 60 to about 70, about 70 to about 200, about 70 to about 175, about 70 to about 150, about 70 to about 100, about 70 to about 90, about 70 to about 80, about 70 to about 75, about 75 to about 200, about 75 to about 175, about 75 to about 150, about 75 to about 100, about 75 to about 90, about 75 to about 80, about 80 to about 200, about 80 to about 175, about 80 to about 150, about 80 to about 100, about 80 to about 90, about 90 to about 200, about 90 to about 175, about 90 to about 150, about 90 to about 100, about 100 to about 200, about 100 to about 175, about 100 to about 150, about 125 to about 200, about 125 to about 175, about 125 to about 150, about 150 to about 200, about 150 to about 175, or about 175 to about 200.

In one embodiment, a polysaccharide disclosed herein has a molecular weight suitable for attachment to a protein while still maintaining a therapeutically useful level of protein activity. In aspects of this embodiment, a polysaccharide disclosed herein has a weight average molecular weight of e.g., about 1 kDa, about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa or about 100 kDa.

In aspects of this embodiment, a polysaccharide disclosed herein has a weight average molecular weight of e.g., at least 1 kDa, at least 2 kDa, at least 3 kDa, at least 4 kDa, at least 5 kDa, at least 6 kDa, at least 7 kDa, at least 8 kDa, at least 9 kDa, at least 10 kDa, at least 11 kDa, at least 12 kDa, at least 13 kDa, at least 14 kDa, at least 15 kDa, at least 16 kDa, at least 17 kDa, at least 18 kDa, at least 19 kDa, at least 20 kDa, at least 21 kDa, at least 22 kDa, at least 23 kDa, at least 24 kDa, at least 25 kDa, at least 26 kDa, at least 27 kDa, at least 28 kDa, at least 29 kDa, at least 30 kDa, at least 31 kDa, at least 32 kDa, at least 33 kDa, at least 34 kDa, at least 35 kDa, at least 40 kDa, at least 45 kDa, at least 50 kDa, at least 55 kDa, at least 60 kDa, at least 65 kDa, at least 70 kDa, at least 75 kDa, at least 80 kDa, at least 85 kDa, at least 90 kDa, at least 95 kDa or at least 100 kDa.

In aspects of this embodiment, a polysaccharide disclosed herein has a weight average molecular weight of e.g., at most 1 kDa, at most 2 kDa, at most 3 kDa, at most 4 kDa, at most 5 kDa, at most 6 kDa, at most 7 kDa, at most 8 kDa, at most 9 kDa, at most 10 kDa, at most 11 kDa, at most 12 kDa, at most 13 kDa, at most 14 kDa, at most 15 kDa, at most 16 kDa, at most 17 kDa, at most 18 kDa, at most 19 kDa, at most 20 kDa, at most 21 kDa, at most 22 kDa, at most 23 kDa, at most 24 kDa, at most 25 kDa, at most 26 kDa, at most 27 kDa, at most 28 kDa, at most 29 kDa, at most 30 kDa, at most 31 kDa, at most 32 kDa, at most 33 kDa, at most 34 kDa, at most 35 kDa, at most 40 kDa, at most 45 kDa, at most 50 kDa, at most 55 kDa, at most 60 kDa, at most 65 kDa, at most 70 kDa, at most 75 kDa, at most 80 kDa, at most 85 kDa, at most 90 kDa, at most 95 kDa or at most 100 kDa.

In other aspects of this embodiment, a polysaccharide disclosed herein has a weight average molecular weight in the range of, e.g., about 2 kDa to about 10 kDa, about 2 kDa to about 15 kDa, about 2 kDa to about 20 kDa, about 2 kDa to about 25 kDa, about 2 kDa to about 30 kDa, about 2 kDa to about 35 kDa, about 2 kDa to about 40 kDa, about 2 kDa to about 45 kDa, about 2 kDa to about 50 kDa, about 2 kDa to about 60 kDa, about 2 kDa to about 70 kDa, about 2 kDa to about 80 kDa, about 2 kDa to about 90 kDa, about 2 kDa to about 100 kDa, about 5 kDa to about 10 kDa, about 5 kDa to about 15 kDa, about 5 kDa to about 20 kDa, about 5 kDa to about 25 kDa, about 5 kDa to about 30 kDa, about 5 kDa to about 35 kDa, about 5 kDa to about 40 kDa, about 5 kDa to about 45 kDa, about 5 kDa to about 50 kDa, about 5 kDa to about 60 kDa, about 5 kDa to about 70 kDa, about 5 kDa to about 80 kDa, about 5 kDa to about 90 kDa, about 5 kDa to about 100 kDa, about 10 kDa to about 15 kDa, about 10 kDa to about 20 kDa, about 10 kDa to about 25 kDa, about 10 kDa to about 30 kDa, about 10 kDa to about 35 kDa, about 10 kDa to about 40 kDa, about 10 kDa to about 45 kDa, about 10 kDa to about 50 kDa, about 10 kDa to about 60 kDa, about 10 kDa to about 70 kDa, about 10 kDa to about 80 kDa, about 10 kDa to about 90 kDa, about 10 kDa to about 100 kDa, about 15 kDa to about 20 kDa, about 15 kDa to about 25 kDa, about 15 kDa to about 30 kDa, about 15 kDa to about 35 kDa, about 15 kDa to about 40 kDa, about 15 kDa to about 45 kDa, about 15 kDa to about 50 kDa, about 15 kDa to about 60 kDa, about 15 kDa to about 70 kDa, about 15 kDa to about 80 kDa, about 15 kDa to about 90 kDa, about 15 kDa to about 100 kDa, about 20 kDa to about 25 kDa, about 20 kDa to about 30 kDa, about 20 kDa to about 35 kDa, about 20 kDa to about 40 kDa, about 20 kDa to about 45 kDa, about 20 kDa to about 50 kDa, about 20 kDa to about 60 kDa, about 20 kDa to about 70 kDa, about 20 kDa to about 80 kDa, about 20 kDa to about 90 kDa, about 20 kDa to about 100 kDa, about 25 kDa to about 30 kDa, about 25 kDa to about 35 kDa, about 25 kDa to about 40 kDa, about 25 kDa to about 45 kDa, about 25 kDa to about 50 kDa, about 25 kDa to about 60 kDa, about 25 kDa to about 70 kDa, about 25 kDa to about 80 kDa, about 25 kDa to about 90 kDa, about 25 kDa to about 100 kDa, about 30 kDa to about 35 kDa, about 30 kDa to about 40 kDa, about 30 kDa to about 45 kDa, about 30 kDa to about 50 kDa, about 30 kDa to about 60 kDa, about 30 kDa to about 70 kDa, about 30 kDa to about 80 kDa, about 30 kDa to about 90 kDa, about 30 kDa to about 100 kDa, about 35 kDa to about 40 kDa, about 35 kDa to about 45 kDa, about 35 kDa to about 50 kDa, about 35 kDa to about 60 kDa, about 35 kDa to about 70 kDa, about 35 kDa to about 80 kDa, about 35 kDa to about 90 kDa, about 35 kDa to about 100 kDa, about 40 kDa to about 45 kDa, about 40 kDa to about 50 kDa, about 40 kDa to about 60 kDa, about 40 kDa to about 70 kDa, about 40 kDa to about 80 kDa, about 40 kDa to about 90 kDa, about 40 kDa to about 100 kDa, about 45 kDa to about 50 kDa, about 45 kDa to about 60 kDa, about 45 kDa to about 70 kDa, about 45 kDa to about 80 kDa, about 45 kDa to about 90 kDa, about 45 kDa to about 100 kDa, about 50 kDa to about 60 kDa, about 50 kDa to about 70 kDa, about 50 kDa to about 80 kDa, about 50 kDa to about 90 kDa, about 50 kDa to about 100 kDa, about 60 kDa to about 70 kDa, about 60 kDa to about 80 kDa, about 60 kDa to about 90 kDa, about 60 kDa to about 100 kDa, about 70 kDa to about 80 kDa, about 70 kDa to about 90 kDa, about 70 kDa to about 100 kDa, about 80 kDa to about 90 kDa, about 80 kDa to about 100 kDa, or about 90 kDa to about 100 kDa.

In one embodiment, a polysialic acid disclosed herein has a molecular weight suitable for attachment to a protein while still maintaining a therapeutically useful level of protein activity. In aspects of this embodiment, a polysialic acid disclosed herein has a weight average molecular weight of e.g., about 1 kDa, about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa or about 100 kDa.

In aspects of this embodiment, a polysialic acid disclosed herein has a weight average molecular weight of e.g., at least 1 kDa, at least 2 kDa, at least 3 kDa, at least 4 kDa, at least 5 kDa, at least 6 kDa, at least 7 kDa, at least 8 kDa, at least 9 kDa, at least 10 kDa, at least 11 kDa, at least 12 kDa, at least 13 kDa, at least 14 kDa, at least 15 kDa, at least 16 kDa, at least 17 kDa, at least 18 kDa, at least 19 kDa, at least 20 kDa, at least 21 kDa, at least 22 kDa, at least 23 kDa, at least 24 kDa, at least 25 kDa, at least 26 kDa, at least 27 kDa, at least 28 kDa, at least 29 kDa, at least 30 kDa, at least 31 kDa, at least 32 kDa, at least 33 kDa, at least 34 kDa, at least 35 kDa, at least 40 kDa, at least 45 kDa, at least 50 kDa, at least 55 kDa, at least 60 kDa, at least 65 kDa, at least 70 kDa, at least 75 kDa, at least 80 kDa, at least 85 kDa, at least 90 kDa, at least 95 kDa or at least 100 kDa.

In aspects of this embodiment, a polysialic acid disclosed herein has a weight average molecular weight of e.g., at most 1 kDa, at most 2 kDa, at most 3 kDa, at most 4 kDa, at most 5 kDa, at most 6 kDa, at most 7 kDa, at most 8 kDa, at most 9 kDa, at most 10 kDa, at most 11 kDa, at most 12 kDa, at most 13 kDa, at most 14 kDa, at most 15 kDa, at most 16 kDa, at most 17 kDa, at most 18 kDa, at most 19 kDa, at most 20 kDa, at most 21 kDa, at most 22 kDa, at most 23 kDa, at most 24 kDa, at most 25 kDa, at most 26 kDa, at most 27 kDa, at most 28 kDa, at most 29 kDa, at most 30 kDa, at most 31 kDa, at most 32 kDa, at most 33 kDa, at most 34 kDa, at most 35 kDa, at most 40 kDa, at most 45 kDa, at most 50 kDa, at most 55 kDa, at most 60 kDa, at most 65 kDa, at most 70 kDa, at most 75 kDa, at most 80 kDa, at most 85 kDa, at most 90 kDa, at most 95 kDa or at most 100 kDa.

In other aspects of this embodiment, a polysialic acid disclosed herein has a weight average molecular weight in the range of, e.g., about 2 kDa to about 10 kDa, about 2 kDa to about 15 kDa, about 2 kDa to about 20 kDa, about 2 kDa to about 25 kDa, about 2 kDa to about 30 kDa, about 2 kDa to about 35 kDa, about 2 kDa to about 40 kDa, about 2 kDa to about 45 kDa, about 2 kDa to about 50 kDa, about 2 kDa to about 60 kDa, about 2 kDa to about 70 kDa, about 2 kDa to about 80 kDa, about 2 kDa to about 90 kDa, about 2 kDa to about 100 kDa, about 5 kDa to about 10 kDa, about 5 kDa to about 15 kDa, about 5 kDa to about 20 kDa, about 5 kDa to about 25 kDa, about 5 kDa to about 30 kDa, about 5 kDa to about 35 kDa, about 5 kDa to about 40 kDa, about 5 kDa to about 45 kDa, about 5 kDa to about 50 kDa, about 5 kDa to about 60 kDa, about 5 kDa to about 70 kDa, about 5 kDa to about 80 kDa, about 5 kDa to about 90 kDa, about 5 kDa to about 100 kDa, about 10 kDa to about 15 kDa, about 10 kDa to about 20 kDa, about 10 kDa to about 25 kDa, about 10 kDa to about 30 kDa, about 10 kDa to about 35 kDa, about 10 kDa to about 40 kDa, about 10 kDa to about 45 kDa, about 10 kDa to about 50 kDa, about 10 kDa to about 60 kDa, about 10 kDa to about 70 kDa, about 10 kDa to about 80 kDa, about 10 kDa to about 90 kDa, about 10 kDa to about 100 kDa, about 15 kDa to about 20 kDa, about 15 kDa to about 25 kDa, about 15 kDa to about 30 kDa, about 15 kDa to about 35 kDa, about 15 kDa to about 40 kDa, about 15 kDa to about 45 kDa, about 15 kDa to about 50 kDa, about 15 kDa to about 60 kDa, about 15 kDa to about 70 kDa, about 15 kDa to about 80 kDa, about 15 kDa to about 90 kDa, about 15 kDa to about 100 kDa, about 20 kDa to about 25 kDa, about 20 kDa to about 30 kDa, about 20 kDa to about 35 kDa, about 20 kDa to about 40 kDa, about 20 kDa to about 45 kDa, about 20 kDa to about 50 kDa, about 20 kDa to about 60 kDa, about 20 kDa to about 70 kDa, about 20 kDa to about 80 kDa, about 20 kDa to about 90 kDa, about 20 kDa to about 100 kDa, about 25 kDa to about 30 kDa, about 25 kDa to about 35 kDa, about 25 kDa to about 40 kDa, about 25 kDa to about 45 kDa, about 25 kDa to about 50 kDa, about 25 kDa to about 60 kDa, about 25 kDa to about 70 kDa, about 25 kDa to about 80 kDa, about 25 kDa to about 90 kDa, about 25 kDa to about 100 kDa, about 30 kDa to about 35 kDa, about 30 kDa to about 40 kDa, about 30 kDa to about 45 kDa, about 30 kDa to about 50 kDa, about 30 kDa to about 60 kDa, about 30 kDa to about 70 kDa, about 30 kDa to about 80 kDa, about 30 kDa to about 90 kDa, about 30 kDa to about 100 kDa, about 35 kDa to about 40 kDa, about 35 kDa to about 45 kDa, about 35 kDa to about 50 kDa, about 35 kDa to about 60 kDa, about 35 kDa to about 70 kDa, about 35 kDa to about 80 kDa, about 35 kDa to about 90 kDa, about 35 kDa to about 100 kDa, about 40 kDa to about 45 kDa, about 40 kDa to about 50 kDa, about 40 kDa to about 60 kDa, about 40 kDa to about 70 kDa, about 40 kDa to about 80 kDa, about 40 kDa to about 90 kDa, about 40 kDa to about 100 kDa, about 45 kDa to about 50 kDa, about 45 kDa to about 60 kDa, about 45 kDa to about 70 kDa, about 45 kDa to about 80 kDa, about 45 kDa to about 90 kDa, about 45 kDa to about 100 kDa, about 50 kDa to about 60 kDa, about 50 kDa to about 70 kDa, about 50 kDa to about 80 kDa, about 50 kDa to about 90 kDa, about 50 kDa to about 100 kDa, about 60 kDa to about 70 kDa, about 60 kDa to about 80 kDa, about 60 kDa to about 90 kDa, about 60 kDa to about 100 kDa, about 70 kDa to about 80 kDa, about 70 kDa to about 90 kDa, about 70 kDa to about 100 kDa, about 80 kDa to about 90 kDa, about 80 kDa to about 100 kDa, or about 90 kDa to about 100 kDa.

A polysaccharide disclosed herein may be covalently-linked to a protein, forming a protein conjugate. The covalent linkage may be an amide linkage between a carboxyl group and an amine group. In an embodiment, the linkage by which the insulin could be covalently bonded to the polysaccharide is via a Schiff base. Suitable groups for conjugating to amines are described further in WO 2006/016168. In an embodiment, a polysaccharide disclosed herein may be covalently-linked to a N-terminus of a protein, forming a N-terminal protein conjugate. In an aspect of this embodiment, a polysialic acid disclosed herein may be covalently-linked to a N-terminus of a protein. In an aspect of this embodiment, a polysialic acid disclosed herein may be covalently-linked to a N-terminus of an insulin or insulin-like protein. In an embodiment, the means of association between the polysaccharide and the insulin is an electrostatic attraction.

In an embodiment, a polysaccharide disclosed herein may be linked to a protein via either its reducing and/or non-reducing terminal unit. In an aspect of this embodiment, a polysaccharide disclosed herein is linked to a protein at both its reducing and non-reducing terminal unit. This means that one polysaccharide chain may be linked to two insulins, i.e. be derivatized at both its reducing and non-reducing end.

A protein disclosed herein may be an insulin or insulin-like protein. Insulin molecule consists of two chains of amino acids linked by disulfide bonds (MW 5804). The beta cells of the pancreatic islets secrete a single chain precursor of insulin, known as proinsulin. Proteolysis of proinsulin results in removal of four basic amino acids (numbers 31, 32, 64 and 65 in the proinsulin chain: Arg, Arg, Lys, Arg respectively) and the connecting ("C") polypeptide. In the resulting two-chain insulin molecule, the A chain has glycine at the amino terminus, and the B chain has phenylalanine at the amino terminus. Insulin may exist as a monomer, dimer or a hexamer formed from three of the dimers. Insulin may be natural, i.e. derived from a human or animal, or synthetic, for instance made by a recombinant method. The hexamer is coordinated with two $Zn^{2+}$ atoms. Biological activity resides in the monomer. The advent of recombinant technology has allowed for the commercial scale manufacture of human insulin (e.g., HUMALIN™ insulin, commercially available from Eli Lilly and Company, Indianapolis, Ind.).

One example of an amino acid sequence for a human insulin precursor or proinsulin is the sequence: MALWMRLLPLLALLALWGPDPAAAFVNQHLCGSHLVEALYLVCGERGFFYTPKTRREAED LQVGQVELGGGPGAGSLQPLALEGSLQKRGIVEQCCTSICSLYQLENYCN (SEQ ID NO: 1). Residues 25-54 of SEQ ID NO: 1 correspond to the B chain and residues 90-110 of SEQ ID NO: 1 correspond to the A chain. One example of an amino acid sequence for an insulin B chain is the sequence: FVNQHLCGSHLVEALYLVCGERGFFYTPKT (SEQ ID NO: 2). One example of an amino acid sequence for an insulin A chain is the sequence: GIVEQCCTSICSLYQLENYCN (SEQ ID NO: 3).

An insulin-like protein has an activity equivalent to that of insulin and may also be referred to as an "insulin-homologue", an "insulin paralog", or an "insulin ortholog." Insulin typically decreases blood glucose concentration. It also increases cell permeability to monosacchorides, amino acids and fatty acids, and accelerates glycolysis, the pentose phosphate cycle, and glycogen synthesis in the liver. In aspects of this embodiment, the insulin-like protein has an activity of, e.g., at least 50%, at least 55%, at least 60%, at least 65%, at least 70%, at least 75%, at least 80%, at least 85%, at least 90%, at least 95%, or at least 99% of human insulin derived from Swissprot accession number P01308.

In certain aspects of this embodiment, the insulin-like protein will comprise an A-chain and a B-Chain linked by one or more disulphide bonds, and comprising the A-chain amino acid sequence of SEQ ID NO: 3 and the B-chain amino acid sequence set forth in SEQ ID NO: 4 depicted below:

FVKQHLCGSHLVEALYLVCGERGFFYTPET (SEQ ID NO: 4)

In certain aspects of this embodiment, the insulin-like protein will comprise an A-chain and a B-Chain linked by one or more disulphide bonds, and comprising the A-chain amino acid sequence of SEQ ID NO: 3 and the B-chain amino acid sequence set forth in SEQ ID NO: 5 depicted below:

FVKQHLCGSHLVEALYLVCGERGFFYTIKT (SEQ ID NO: 5)

In certain aspects of this embodiment, the insulin-like protein will comprise an A-chain and a B-Chain linked by one or more disulphide bonds, and comprising the A-chain amino acid sequence of SEQ ID NO: 3 and the B-chain amino acid sequence set forth in SEQ ID NO: 6 depicted below:

FVNQHLCGSHLVEALYLVCGERGFFYTDKT (SEQ ID NO: 6)

In certain aspects of this embodiment, the insulin-like protein will comprise an A-chain and a B-Chain linked by one or more disulphide bonds, and comprising the A-chain amino acid sequence of SEQ ID NO: 3 and the B-chain amino acid sequence set forth in SEQ ID NO: 7 depicted below:

FVNQHLCGSDLVEALYLVCGERGFFYTPKT (SEQ ID NO: 7)

In certain aspects of this embodiment, the insulin-like protein will comprise an A-chain and a B-Chain linked by one or more disulphide bonds, and comprising the A-chain amino acid sequence of SEQ ID NO: 3 and the B-chain amino acid sequence set forth in SEQ ID NO: 8 depicted below:

FVNQHLCGSHLVEALYLVCGERGFFYTKPT (SEQ ID NO: 8)

Besides exhibiting insulin activity, an insulin-like protein may also be identified by having high amino acid sequence identity to an insulin. Whether two sequences have high sequence identity (or homology) is routinely calculated using a percentage similarity or identity, terms that are well known in the art. Sequences for an insulin-like protein may be compared to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. The term "percent (%) amino acid sequence identity" with respect to any of SEQ ID NOS: 1-8 is defined as the percentage of amino acid residues in a candidate sequence that are identical with the amino acid residues in any of SEQ ID NOS: 1-8 amino acid sequence, after aligning the sequences and introducing gaps, if necessary, to achieve the maximum percent sequence identity, and not considering any conservative substitutions as part of the sequence identity. Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., *Align-M—A New Algorithm for Multiple Alignment of Highly Divergent Sequences*, 20(9) Bioinformatics, 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

In aspects of this embodiment, an insulin-like protein disclosed herein has an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. In other aspects of this embodiment, an insulin-like protein disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

In other aspects of this embodiment, an insulin-like protein disclosed herein has, e.g., at least 1, at least 2, at least 3, at least 4, at least 5, at least 6, at least 7, at least 8, at least 9, at least 10, at least 11, at least 12, at least 13, at least 14, or at least 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8; or at most 1, at most 2, at most 3, at most 4, at most 5, at most 6, at most 7, at most 8, at most 9, at most 10, at most 11, at most 12, at most 13, at most 14, or at most 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. In yet other aspects of this embodiment, an insulin-like protein disclosed herein has, e.g., at least 1, at least 2, at least 3, at least 4, at least 5, at least 6, at least 7, at least 8, at least 9, at least 10, at least 11, at least 12, at least 13, at least 14, or at least 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8; or at most 1, at most 2, at most 3, at most 4, at most 5, at most 6, at most 7, at most 8, at most 9, at most 10, at most 11, at most 12, at most 13, at most 14, or at most 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

The present specification describes various polypeptide variants where one amino acid is substituted for another, such as, e.g., an insulin-like protein disclosed herein. A substitution can be assessed by a variety of factors, such as, e.g., the physic properties of the amino acid being substituted (Table 1) or how the original amino acid would tolerate a substitution (Table 2). The selections of which amino acid can be substituted for another amino acid in a polypeptide are known to a person of ordinary skill in the art.

TABLE 1

Amino Acid Properties

| Property | Amino Acids |
|---|---|
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

Amino Acid Substitutions

| Amino Acid | Favored Substitution | Neutral Substitutions | Disfavored substitution |
|---|---|---|---|
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |

TABLE 2-continued

Amino Acid Substitutions

| Amino Acid | Favored Substitution | Neutral Substitutions | Disfavored substitution |
|---|---|---|---|
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

In aspects of this embodiment, a hydrophic amino acid at one particular position in an insulin-like protein disclosed herein can be substituted with another hydrophic amino acid. Examples of hydrophic amino acids include, e.g., C, F, I, L, M, V and W. In another aspect of this embodiment, an aliphatic amino acid at one particular position in an insulin-like protein disclosed herein can be substituted with another aliphatic amino acid. Examples of aliphatic amino acids include, e.g., A, I, L, P, and V. In yet another aspect of this embodiment, an aromatic amino acid at one particular position in an insulin-like protein disclosed herein can be substituted with another aromatic amino acid. Examples of aromatic amino acids include, e.g., F, H, W and Y. In still another aspect of this embodiment, a stacking amino acid at one particular position in an insulin-like protein disclosed herein can be substituted with another stacking amino acid. Examples of stacking amino acids include, e.g., F, H, W and Y. In a further aspect of this embodiment, a polar amino acid at one particular position in an insulin-like protein disclosed herein can be substituted with another polar amino acid. Examples of polar amino acids include, e.g., D, E, K, N, Q, and R. In a further aspect of this embodiment, a less polar or indifferent amino acid at one particular position in an insulin-like protein disclosed herein can be substituted with another less polar or indifferent amino acid. Examples of less polar or indifferent amino acids include, e.g., A, H, G, P, S, T, and Y. In a yet further aspect of this embodiment, a positive charged amino acid at one particular position in an insulin-like protein disclosed herein can be substituted with another positive charged amino acid. Examples of positive charged amino acids include, e.g., K, R, and H. In a still further aspect of this embodiment, a negative charged amino acid at one particular position in an insulin-like protein disclosed herein can be substituted with another negative charged amino acid. Examples of negative charged amino acids include, e.g., D and E. In another aspect of this embodiment, a small amino acid at one particular position in an insulin-like protein disclosed herein can be substituted with another small amino acid. Examples of small amino acids include, e.g., A, D, G, N, P, S, and T. In yet another aspect of this embodiment, a C-beta branching amino acid at one particular position in an insulin-like protein disclosed herein can be substituted with another C-beta branching amino acid. Examples of C-beta branching amino acids include, e.g., I, T and V.

The pharmaceutical compositions disclosed herein are formulated to be administered intranasally. The pharmaceutical compositions disclosed herein may be liquid, e.g. adapted for administration as a spray. Liquid preparations, such as those based on aqueous formulations, will usually include ancillary agents, for example a pH-buffering system, preferably a buffer such as phosphate, borate, citrate or acetate buffers, a preservative and an osmotic pressure controlling agent, e.g. glycerol or sodium chloride. For instance, boric acid, sodium bicarbonate, sodium phosphate monobasic, sodium phosphate dibasic, and sodium phosphate dibasic heptahydrate may be used as buffering agents. Furthermore, boric acid and sodium bicarbonate may be used together in a buffer system; sodium phosphate monobasic and sodium phosphate dibasic may be used together in a buffer system; and sodium phosphate dibasic heptahydrate may be used in a buffer system.

Preferred liquid preparations are those in which the diluent is water. Such preparations may be prepared by dispersing the pharmaceutically active agent and ancillary agents, the dispersion being conducted by any method usually employed for suspension or emulsification, e.g. ultrasonic treatment. Adjustment of the aqueous phase to neutrality (i.e. to pH in the range from about 6.5 to about 8) may be accomplished in any of the preparatory steps. Preferably, microemulsions are prepared in which the size of the dispersed particles or droplets is of the order of 10 nm, thereby facilitating their passage across the nasal mucosa. Such microemulsions may be sterilized by filtration.

Pharmaceutically acceptable excipients, including dispersing agents, isotonicity agents, stabilizing agents and the like are used as appropriate in the pharmaceutical compositions disclosed herein. Remington's Pharmaceutical Sciences, Mack Publishing Co., Easton, Pa., latest edition, incorporated herein by reference, provides a compendium of formulation techniques as are generally known to practitioners. The Handbook of Pharmaceutical Excipients, Pharmaceutical Press, Grayslake, Ill., latest edition, incorporated herein by reference, provides a compendium of pharmaceutically acceptable excipients that may be used in the pharmaceutical compositions disclosed herein.

The pharmaceutical compositions disclosed herein may contain excipients such as, for example, antioxidants, preservatives, buffering agents, agents that increase viscosity, diluents, pH adjusters, and solvents.

Antioxidants are substances that prevent oxidation of the formulations. Suitable antioxidants for use in the compositions disclosed herein include, but are not limited to, butylated hydroxytoluene, butylated hydroxyanisole, potassium metabisulfite, and the like.

In some embodiments disclosed herein, the composition contains a preservative that is chosen in quantities that preserve the composition, but do not cause irritation of the nasal mucosa. Suitable preservatives for use in some embodiments of the compositions disclosed herein include, but are not limited to, m-cresol, benzalkonium chloride, methyl, ethyl, propyl or butylparaben, benzyl alcohol, phenylethyl alcohol, benzethonium, or combination thereof.

If a buffering agent is employed in the composition, it is chosen in quantities that preferably do not irritate the nasal mucosa. Buffering agents include agents that reduce pH changes. Preferred buffering agents for use in the present invention include, but are not limited to, salts of borate, citrate, acetate, or phosphate. The most preferred buffers include boric acid and sodium bicarbonate, sodium phosphate heptahydrate, sodium phosphate monobasic and sodium phosphate dibasic, sodium citrate, sodium acetate, potassium dihydrogen phosphate, and a citrate buffer comprising sodium citrate and citric acid.

The pharmaceutical compositions disclosed herein may include one or more agents that increase viscosity chosen in quantities that preferably do not irritate the nasal mucosa and increase nasal retention time. Preferred agents that increase viscosity include, but are not limited to, methylcellulose, carboxymethylcellulose sodium, ethylcellulose, carrageenan, carbopol, and/or combinations thereof.

Suitable diluents include aqueous or non-aqueous diluents or combination thereof. Examples of aqueous diluents include, but are not limited to, saline, water, dextrose or combinations thereof. Non-aqueous diluents include, but are not limited to, alcohols, particularly polyhydroxy alcohols such as propylene glycol, polyethylene glycol, glycerol, and vegetable and mineral oils. These aqueous and/or non-aqueous diluents can be added in various concentrations and combinations to form solutions, suspensions, oil-in-water emulsions or water-in-oil emulsions.

The pH of the compositions disclosed herein may be adjusted to the desired value using any suitable organic or inorganic acid or organic or inorganic base. Suitable organic acids include, but are not limited to, acetic acid, citric acid, glutamic acid and methane sulfonic acid. Suitable inorganic acids include, but are not limited to, hydrochloric acid and sulphuric acid. Suitable organic bases include, but are not limited to, meglumine, lysine and tromethamine (TRIS). Suitable inorganic bases include, but are not limited to, sodium hydroxide and potassium hydroxide.

Solvents that may be used to prepare the compositions disclosed herein include, but are not limited to, water, ethanol, propylene glycol, polyethylene glycol, glycerin, phenol, glycofurol, benzyl benzoate and polyoxyethylene castor oil derivatives.

The pharmaceutical compositions disclosed herein may contain other pharmaceutically acceptable ingredients well known in the art. Such excipients include, but are not limited to, chelating agents (such as edetic acid or one of its salts), flavors, sweeteners, thickening, adhesive or gelling agents, including, but not limited to, celluloses such as hydroxypropyl methylcellulose, methylcellulose, hydroxypropyl cellulose, sodium carboxyl cellulose and microcrystalline cellulose, poloxomers, polyethylene glycols, carbomers or polyethylene oxide.

The concentration of the pharmaceutically active agent in the preparations of this invention will depend on the particular agent chosen, on its efficacy, on a comparison of its bioavailability by nasal administration and by other routes of administration, for example parenteral injection, and on the desired frequency of administration combined with the desired single dosage of the formulation. Such pharmacological data can routinely be obtained by the skilled artisan from animal experiments, for example in terms of index values.

The pharmaceutical compositions disclosed herein may be used in any dosage dispensing device adapted for intranasal administration. The device should be constructed with a view to ascertaining optimum metering accuracy and compatibility of its constructive elements. The compositions may be administered as drops, sprays, aerosols or by any other intranasal dosage form. Optionally, the delivery system may be a unit dose delivery system. The volume of solution or suspension delivered per dose may be anywhere from 10 µL to 1000 µL and preferably between 50 µL and 300 µL. Delivery systems for these various dosage forms may be dropper bottles, plastic squeeze units, atomizers, nebulizers, metered nasal sprayers, or pharmaceutical aerosols in either unit dose or multiple dose packages. Aerosol systems require a propellant to be inert towards the formulation. Suitable propellants may be selected among such gases as fluorocarbons, hydrocarbons, nitrogen and dinitrogen oxide or mixtures thereof.

A preferred method of administering the solutions disclosed herein is using a spray device. Spray devices can be single ("unit") dose or multiple dose systems, for example comprising a bottle, pump and actuator, and are available from various commercial sources.

For a spray device, the typical volume of liquid that is dispensed in a single spray actuation is from 0.01 to 0.14 ml, for example from 0.05 to 0.14 ml, such as 0.1 ml. It is a practical proposition to administer up to about 0.2 ml into each nostril (i.e. 2×0.1 ml sprays) to provide a therapeutic dose of drug, although the most acceptable dosing regimen would be one spray into one or both nostrils.

The invention also provides a nasal drug delivery device or a dose cartridge for use in a nasal delivery device loaded with a composition disclosed herein.

In another aspect, the present specification provides a method of treating insulin resistance in a subject, comprising administering to the brain of said subject a pharmaceutical composition comprising a therapeutically effective amount of polysaccharide derivatized insulin protein, wherein said administration results in a amelioration or slowing of the progression of a symptom associated with insulin resistance. In an embodiment, the pharmaceutical composition will be effective treating insulin resistance associated with, e.g., type-2 diabetes, obesity, systemic inflammation, chronic pancreatitis, hypertension, hyperglycycemia, dyslipidemia, promoting weight loss, gestational diabetes, colon cancer, prostate cancer, pancreatic cancer, chronic liver disease, and hepatitis C virus (HCV) infection in a mammalian subject.

In another aspect, the present invention provides a method of treating a neurological disorder in a subject, the method comprising administering to the brain of said subject a pharmaceutical composition comprising a therapeutically effective amount of polysaccharide derivatized insulin protein, wherein said administration results in the amelioration, slowing of the progression, or delay of onset of a neurological disorder.

In certain embodiments, the neurological or CNS disorders include, but are not limited to, memory disorders, head injury, spinal cord injury, seizures, stroke, dementia, memory loss, attention deficit disorder (ADD), epilepsy, and ischemia.

In certain embodiments, the neurological disorder is a neurodegenerative disease including, but not limited to, Amyotrophic Lateral Sclerosis (ALS), multiple sclerosis, Huntington's disease, Parkinson's disease and Alzheimer's disease.

In certain embodiments, the neurological disorders include CNS damage resulting from infectious diseases such as viral encephalitis, bacterial or viral meningitis, CNS damage from tumors, and mental disorders such as mood disorders (i.e., depression, bipolar disorder), anxiety disorders, memory disorders and schizophrenic disorders.

The effectiveness of the pharmaceutical compositions disclosed herein for the above methods can be shown by utilizing known models for neurodegenerative diseases such as Alzheimer's disease, stroke, Parkinson's disease, multiple sclerosis, spinal cord injuries, traumatic brain injuries and other nervous system and systemic diseases, in addition to local diseases. For example, an accepted model for neurodegenerative disorders such as Alzheimer's disease utilizes the senescence accelerated mouse, SAMP8 (Morley et al, The senescence accelerated mouse (SAMPi) as a model for oxidative stress and Alzheimer's disease, Biochimica et Biophysica Act 1882 (2012) 650-656).

In certain embodiments, the insulin or insulin-like protein may be provided in the present pharmaceutical compositions at a dose per volume of from 0 to 200 IU/ml, 100 to 300 IU/ml, 300 to 500 IU/ml, or 500 IU/ml to 1000 IU/ml, which will provide 0-20 IU/0.1 ml, 10-30 IU/0.1 ml, 30-50 IU/0.1 ml, and 50-100 IU/0.1 ml, respectively, as needed. In certain embodiments, the insulin may be provided in the present pharmaceutical composition at a dose per volume of from 50 to 150 IU/ml, 150 to 250 IU/ml, and 350 to 450 IU/ml which will provide 5-15 IU/0.1 ml, 15-25 IU/0.1 ml, and 35-45 IU/0.1 ml respectively as needed. I certain embodiments, the insulin may be provided in the present pharmaceutical composition at a dose per volume of about 100 IU/ml, about 200 IU/ml, about 400 IU/ml, or about 500 IU/ml, which will provide about 10 IU/0.1 ml, about 20 IU/0.1 ml, about 40 IU/0.1 ml, and about 50 IU/0.1 ml, respectively, as needed. A therapeutic dose for the recombinant insulin is approximately 20-40 IU/day. A suitable dose range for recombinant insulin is approximately 10-80 IU/day.

In another aspect, the present invention provides a method for producing a polysaccharide derivative of insulin wherein an anionic polysaccharide comprising 2-125 saccharide units is chemically reacted substantially only at the N-terminal amine of the therapeutic agent.

In an embodiment, the anionic polysaccharide has been activated before derivatisation to the therapeutic agent. It may, for instance, have a reactive aldehyde group and the derivatisation reaction may be carried out under reducing conditions. The reactive aldehyde group may be produced by controlled oxidation of a hydroxyl group of the polysaccharide. In an embodiment, the reactive aldehyde is generated in a preliminary step, in which the polysaccharide is reacted under controlled oxidation conditions, for instance using sodium periodate, in aqueous solution. In an embodiment, the oxidation is a chemical oxidation, although enzymes which are capable of carrying out this step may also be used. The reactive aldehyde group may be at the non-reducing end or reducing end of the polysaccharide. The therapeutic agent, typically the N-terminus, may then react with the reactive aldehyde group to produce an adduct which, when reduced, produces the N-terminal derivative of therapeutic agent.

In an embodiment, the activation of the polysaccharide should will be carried out under conditions such that there is substantially no mid-chain cleavage of the backbone of the polysaccharide, that is substantially no molecular weight reduction. The oxidant is suitably perrhuthenate, or, preferably, periodate. Oxidation may be carried out with periodate at a concentration in the range 1 mM to 1M, at a pH in the range 3 to 10, a temperature in the range 0° to 60° C. for a time in the range 1 min to 48 hours.

Suitable reduction conditions for the derivatisation reaction may utilise hydrogen with catalysts or, preferably hydrides, such as borohydrides. These may be immobilised such as AMBERLITE™-supported borohydride. In an embodiment, alkali metal hydrides such as sodium borohydride is used as the reducing agent, at a concentration in the range 1 µM to 0.1M, a pH in the range 4 to 10, a temperature in the range 0 to 60° C. and a period in the range 1 min to 72 hours. The reaction conditions are selected such that pendant carboxyl groups on the starting material are not reduced. Other suitable reducing agents are cyanoborohydride under acidic conditions, e.g. polymer supported cyanoborohydride or alkali metal cyanoborohydride, L-ascorbic acid, sodium metabisulphite, L-selectride, triacetoxyborohydride etc.

Other activated derivatives of polysaccharides may have utility in the present invention, including those with pendant functional groups such as NHS, as described in our earlier patent application WO 06/00540.

In one embodiment, the reactive aldehyde is at the reducing end of the polysaccharide and the non-reducing end has been passivated such that it does not react with pendant groups on the insulin.

Chemistry suitable for preparing a polysaccharide with a reactive aldehyde at the reducing terminal of a polysaccharide is described in our earlier application WO 05/016974. The process involves a preliminary selective oxidation step followed by reduction and then further oxidation to produce a compound with an aldehyde at the reducing terminal and a passivated non-reducing end.

WO 2005/016973 describes polysialic acid derivatives that are useful for conjugation to proteins, particularly those which have free sulfhydryl drugs. The polysialic acid compound is reacted with a heterobifunctional reagent to introduce a pendant functional group for site-specific conjugation to sulfhydryl groups. The anionic polysaccharides used in the present invention may also be derivatized with a heterobifunctional reagent in this manner.

We have found that certain reaction conditions promote selective derivatisation at the N-terminal of the insulin. To promote selective reaction at the N-terminal, the derivatisation reaction should be carried out in a first aqueous solution of acidic pH, and the resultant polysaccharide derivative should then be purified in a second aqueous solution of higher pH than the first aqueous solution. By acidic pH we mean a pH less than 7. Typically the pH of the first aqueous solution is in the range 4.0-6.5, preferably 4.0-6.0 and the pH of the second aqueous solution is in the range of 6.5-9.0, preferably 6.5-8.5 or 6.5-8.0. The low pH of the derivatisation reaction promotes selective derivatisation at the N-terminus of the protein rather than at any mid-chain sites.

Furthermore, we have found that the use of certain formulation additives promotes the formation of a selective, stable, polysaccharide therapeutic agent-derivative. The formulation additive may be selected from one or more buffers, stabilisers, surfactants, salts, polymers, metal ions, sugars, polyols or amino acids. These may be added to the reaction medium, or alternatively may be added to the final product composition, as a stabiliser.

In one embodiment of this invention, the formulation additive is sorbitol, trehalose or sucrose. In a different embodiment, the formulation additive is a non-ionic surfactant. The formulation additive may alternatively be a polymer selected from PSA, PEG or hydroxy-beta-cyclodextrin. In a different embodiment the formulation additive is a divalent metal ion. In an embodiment, the divalent metal ions include $Zn^{2+}$, $Ni^{2+}$, $Co^{2+}$, $Sr^{2+}$ or $Fe^{2+}$.

The formulation additive may be a buffer. Preferably when the formulation additive is a buffer, it is sodium phosphate or sodium acetate.

The purification of the polysaccharide derivative in the method of the present invention may be carried out using a variety of methods known in the art. Examples of suitable purification methods include HIC (hydrophobic interaction chromatography), SEC (size exclusion chromatography), HPLC (high performance liquid chromatography), and IEC (ion exchange chromatography).

A population of polysialic acids having a wide molecular weight distribution may be fractionated into fractions with lower polydispersities, i.e. into fractions with differing average molecular weights. Fractionation is preferably performed by anion exchange chromatography, using for elution a suitable basic buffer, as described in our earlier patent applications WO 2005/016794 and WO 2005/03149. The fractionation method is suitable for a polysaccharide starting material as well as to the derivatives. The technique may thus be applied before or after the essential process steps of this invention. In an embodiment, the resultant polysaccharide derivative of insulin has a polydispersity of less than 1.1.

Importantly, the polysaccharides used to prepare the polysaccharide derivatives disclosed herein demonstrate the ability to facilitate transport of insulin across the nasal mucosa, suggesting that such polysaccharides may be "enhancing agents" that could facilitate transport of therapeutic agents across a variety of mucosa barriers. In an embodiment, the mucosa barrier includes the nasal, oral, intestinal, buccal, bronchopulmonary, vaginal, and rectal mucosal surfaces and includes all mucus-secreting membranes lining all body cavities or passages that communicate with the exterior.

Aspects of the present invention can also be described as follows:

1. A method of administering a therapeutically effective amount of a protein to the brain of an individual, the method comprising intranasal administration of a pharmaceutical composition comprising a population of the protein attached with a polysaccharide.
2. The method according to embodiment 1, wherein the protein is an insulin and/or an insulin-like protein.
3. The method according to embodiment 2, wherein the insulin is a natural insulin derived from an animal or a synthetic insulin.
4. The method according to embodiment 3, wherein the natural insulin is derived from a human.
5. The method according to any one of embodiments 2-4, wherein the insulin comprised SEQ ID NO: 1, SEQ ID NO: 2, or SEQ ID NO: 3.
6. The method according to any one of embodiments 2-5, wherein the insulin-like protein is a homolog, paralog, or ortholog of insulin.
7. The method according to any one of embodiments 2-6, wherein the insulin-like protein has an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.
8. The method according to any one of embodiments 2-7, wherein the insulin-like protein has an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.
9. The method according to any one of embodiments 2-8, wherein the insulin-like protein has at least 1, at least 2, at least 3, at least 4, at least 5, at least 6, at least 7, at least 8, at least 9, at least 10, at least 11, at least 12, at least 13, at least 14, or at least 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.
10. The method according to any one of embodiments 2-8, wherein the insulin-like protein has at most 1, at most 2, at most 3, at most 4, at most 5, at most 6, at most 7, at most 8, at most 9, at most 10, at most 11, at most 12, at most 13, at most 14, or at most 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.
11. The method according to any one of embodiments 2-10, wherein the insulin-like protein has at least 1, at least 2, at least 3, at least 4, at least 5, at least 6, at least 7, at least 8, at least 9, at least 10, at least 11, at least 12, at least 13, at least 14, or at least 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8;
12. The method according to any one of embodiments 2-10, wherein the insulin-like protein has at most 1, at most 2, at most 3, at most 4, at most 5, at most 6, at most 7, at most 8, at most 9, at most 10, at most 11, at most 12, at most 13, at most 14, or at most 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.
13. The method according to any one of embodiments 2-10, wherein the insulin-like protein comprises the A-chain/B-chain amino acid sequence combinations of SEQ ID NO: 3/SEQ ID NO: 4, or SEQ ID NO: 3/SEQ ID NO: 5, or SEQ ID NO: 3/SEQ ID NO: 6, or SEQ ID NO: 3/SEQ ID NO: 7, or SEQ ID NO: 3/SEQ ID NO: 8.
14. The method according to any one of embodiments 1-13, wherein the polysaccharide is an anionic polysaccharide.
15. The method according to any one of embodiments 2-14, wherein the anionic polysaccharide is a polysialic acid, a heparin, a hyaluronic acid and a chondroitin sulphate.
16. The method according to embodiment 15, wherein the polysialic acid is derived from a bacterial source or a mammalian source.
17. The method according to embodiment 16, wherein the bacterial source is a polysaccharide B of *E. coli* KI, *N. meningitidis, Maraxella liquefaciens* or *Pasteurella aeruginosa*, a K92 polysaccharide from *E. coli* K92 strain, or a C polysaccharides of *N. meningitides.*
18. The method according to any one of embodiments 15-17, wherein the polysialic acid is a homopolymeric form, a heteropolymeric form, or a co-polymer form.
19. The method according to any one of embodiments 14-18, wherein the anionic polysaccharide consists substantially only of sialic acid units.
20. The method according to any one of embodiments 14-18, wherein the anionic polysaccharide has both sialic acid units and saccharide units other than sialic acid in the molecule.
21. The method according to any one of embodiments 1-20, wherein the polysaccharide comprises about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 150, about 175, or about 200 saccharide units.

22. The method according to any one of embodiments 1-20, wherein the polysaccharide comprises at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 150, at least 175, or at least 200 saccharide units.

23. The method according to any one of embodiments 1-20, wherein the polysaccharide comprises about at most 2, at most 3, at most 4, at most 5, at most 6, at most 7, at most 8, at most 9, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95, at most 100, at most 105, at most 110, at most 115, at most 120, at most 125, at most 150, at most 175, or at most 200 saccharide units.

24. The method according to any one of embodiments 1-20, wherein the polysaccharide comprises about 2 to about 200, about 2 to about 175, about 2 to about 150, about 2 to about 125, about 2 to about 100, about 2 to about 90, about 2 to about 80, about 2 to about 75, about 2 to about 70, about 2 to about 60, about 2 to about 50, about 2 to about 40, about 2 to about 30, about 2 to about 25, about 2 to about 20, about 2 to about 15, about 2 to about 10, about 5 to about 200, about 5 to about 175, about 5 to about 150, about 5 to about 125, about 5 to about 100, about 5 to about 90, about 5 to about 80, about 5 to about 75, about 5 to about 70, about 5 to about 60, about 5 to about 50, about 5 to about 40, about 5 to about 30, about 5 to about 25, about 5 to about 20, about 5 to about 15, about 5 to about 10, about 10 to about 200, about 10 to about 175, about 10 to about 150, about 10 to about 125, about 10 to about 100, about 10 to about 90, about 10 to about 80, about 10 to about 75, about 10 to about 70, about 10 to about 60, about 10 to about 50, about 10 to about 40, about 10 to about 30, about 10 to about 25, about 10 to about 20, about 10 to about 15, about 20 to about 200, about 20 to about 175, about 20 to about 150, about 20 to about 100, about 20 to about 90, about 20 to about 80, about 20 to about 75, about 20 to about 70, about 20 to about 60, about 20 to about 50, about 20 to about 40, about 20 to about 30, about 30 to about 200, about 30 to about 175, about 30 to about 150, about 30 to about 100, about 30 to about 90, about 30 to about 80, about 30 to about 75, about 30 to about 70, about 30 to about 60, about 30 to about 50, about 30 to about 40, about 40 to about 200, about 40 to about 175, about 40 to about 150, about 40 to about 100, about 40 to about 90, about 40 to about 80, about 40 to about 75, about 40 to about 70, about 40 to about 60, about 40 to about 50, about 50 to about 200, about 50 to about 175, about 50 to about 150, about 50 to about 100, about 50 to about 90, about 50 to about 80, about 50 to about 75, about 50 to about 70, about 50 to about 60, about 60 to about 200, about 60 to about 175, about 60 to about 150, about 60 to about 100, about 60 to about 90, about 60 to about 80, about 60 to about 75, about 60 to about 70, about 70 to about 200, about 70 to about 175, about 70 to about 150, about 70 to about 100, about 70 to about 90, about 70 to about 80, about 70 to about 75, about 75 to about 200, about 75 to about 175, about 75 to about 150, about 75 to about 100, about 75 to about 90, about 75 to about 80, about 80 to about 200, about 80 to about 175, about 80 to about 150, about 80 to about 100, about 80 to about 90, about 90 to about 200, about 90 to about 175, about 90 to about 150, about 90 to about 100, about 100 to about 200, about 100 to about 175, about 100 to about 150, about 125 to about 200, about 125 to about 175, about 125 to about 150, about 150 to about 200, about 150 to about 175, or about 175 to about 200, saccharide units.

25. The method according to any one of embodiments 1-24, wherein the polysaccharide has a weight average molecular weight of about 1 kDa, about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa or about 100 kDa.

26. The method according to any one of embodiments 1-24, wherein the polysaccharide has a weight average molecular weight of at least 1 kDa, at least 2 kDa, at least 3 kDa, at least 4 kDa, at least 5 kDa, at least 6 kDa, at least 7 kDa, at least 8 kDa, at least 9 kDa, at least 10 kDa, at least 11 kDa, at least 12 kDa, at least 13 kDa, at least 14 kDa, at least 15 kDa, at least 16 kDa, at least 17 kDa, at least 18 kDa, at least 19 kDa, at least 20 kDa, at least 21 kDa, at least 22 kDa, at least 23 kDa, at least 24 kDa, at least 25 kDa, at least 26 kDa, at least 27 kDa, at least 28 kDa, at least 29 kDa, at least 30 kDa, at least 31 kDa, at least 32 kDa, at least 33 kDa, at least 34 kDa, at least 35 kDa, at least 40 kDa, at least 45 kDa, at least 50 kDa, at least 55 kDa, at least 60 kDa, at least 65 kDa, at least 70 kDa, at least 75 kDa, at least 80 kDa, at least 85 kDa, at least 90 kDa, at least 95 kDa or at least 100 kDa.

27. The method according to any one of embodiments 1-24, wherein the polysaccharide has a weight average molecular weight at most 1 kDa, at most 2 kDa, at most 3 kDa, at most 4 kDa, at most 5 kDa, at most 6 kDa, at most 7 kDa, at most 8 kDa, at most 9 kDa, at most 10 kDa, at most 11 kDa, at most 12 kDa, at most 13 kDa, at most 14 kDa, at most 15 kDa, at most 16 kDa, at most 17 kDa, at most 18 kDa, at most 19 kDa, at most 20 kDa, at most 21 kDa, at most 22 kDa, at most 23 kDa, at most 24 kDa, at most 25 kDa, at most 26 kDa, at most 27 kDa, at most 28 kDa, at most 29 kDa, at most 30 kDa, at most 31 kDa, at most 32 kDa, at most 33 kDa, at most 34 kDa, at most 35 kDa, at most 40 kDa, at most 45 kDa, at most 50 kDa, at most 55 kDa, at most 60 kDa, at most 65 kDa, at most 70 kDa, at most 75 kDa, at most 80 kDa, at most 85 kDa, at most 90 kDa, at most 95 kDa or at most 100 kDa.

28. The method according to any one of embodiments 1-24, wherein the polysaccharide has a weight average molecular weight in the range of about 2 kDa to about 10 kDa, about 2 kDa to about 15 kDa, about 2 kDa to about 20 kDa, about 2 kDa to about 25 kDa, about 2 kDa to about 30 kDa, about 2 kDa to about 35 kDa, about 2 kDa to about 40 kDa, about 2 kDa to about 45 kDa, about 2 kDa to about 50 kDa, about 2 kDa to about 60 kDa, about 2 kDa to about 70 kDa, about 2 kDa to about 80 kDa, about 2 kDa to about 90 kDa, about 2 kDa to about 100 kDa, about 5 kDa to about 10 kDa, about 5 kDa to about 15 kDa, about 5 kDa to about 20 kDa, about 5 kDa to about 25 kDa, about 5 kDa to about 30 kDa, about 5 kDa to about 35 kDa, about 5 kDa to about 40 kDa, about 5 kDa to about 45 kDa, about 5 kDa to about 50 kDa, about 5 kDa to about 60 kDa, about 5 kDa to about 70 kDa, about 5 kDa to about 80 kDa, about 5 kDa to about 90 kDa, about 5 kDa to about 100 kDa, about 10 kDa to about 15 kDa, about 10 kDa to about 20 kDa, about 10 kDa to about 25 kDa, about 10 kDa to about 30 kDa, about 10 kDa to about 35 kDa, about 10 kDa to about 40 kDa, about 10 kDa to about 45 kDa, about 10 kDa to about 50 kDa, about 10 kDa to about 60 kDa, about 10 kDa to about 70 kDa, about 10 kDa to about 80 kDa, about 10 kDa to about 90 kDa, about 10 kDa to about 100 kDa, about 15 kDa to about 20 kDa, about 15 kDa to about 25 kDa, about 15 kDa to about 30 kDa, about 15 kDa to about 35 kDa, about 15 kDa to about 40 kDa, about 15 kDa to about 45 kDa, about 15 kDa to about 50 kDa, about 15 kDa to about 60 kDa, about 15 kDa to about 70 kDa, about 15 kDa to about 80 kDa, about 15 kDa to about 90 kDa, about 15 kDa to about 100 kDa, about 20 kDa to about 25 kDa, about 20 kDa to about 30 kDa, about 20 kDa to about 35 kDa, about 20 kDa to about 40 kDa, about 20 kDa to about 45 kDa, about 20 kDa to about 50 kDa, about 20 kDa to about 60 kDa, about 20 kDa to about 70 kDa, about 20 kDa to about 80 kDa, about 20 kDa to about 90 kDa, about 20 kDa to about 100 kDa, about 25 kDa to about 30 kDa, about 25 kDa to about 35 kDa, about 25 kDa to about 40 kDa, about 25 kDa to about 45 kDa, about 25 kDa to about 50 kDa, about 25 kDa to about 60 kDa, about 25 kDa to about 70 kDa, about 25 kDa to about 80 kDa, about 25 kDa to about 90 kDa, about 25 kDa to about 100 kDa, about 30 kDa to about 35 kDa, about 30 kDa to about 40 kDa, about 30 kDa to about 45 kDa, about 30 kDa to about 50 kDa, about 30 kDa to about 60 kDa, about 30 kDa to about 70 kDa, about 30 kDa to about 80 kDa, about 30 kDa to about 90 kDa, about 30 kDa to about 100 kDa, about 35 kDa to about 40 kDa, about 35 kDa to about 45 kDa, about 35 kDa to about 50 kDa, about 35 kDa to about 60 kDa, about 35 kDa to about 70 kDa, about 35 kDa to about 80 kDa, about 35 kDa to about 90 kDa, about 35 kDa to about 100 kDa, about 40 kDa to about 45 kDa, about 40 kDa to about 50 kDa, about 40 kDa to about 60 kDa, about 40 kDa to about 70 kDa, about 40 kDa to about 80 kDa, about 40 kDa to about 90 kDa, about 40 kDa to about 100 kDa, about 45 kDa to about 50 kDa, about 45 kDa to about 60 kDa, about 45 kDa to about 70 kDa, about 45 kDa to about 80 kDa, about 45 kDa to about 90 kDa, about 45 kDa to about 100 kDa, about 50 kDa to about 60 kDa, about 50 kDa to about 70 kDa, about 50 kDa to about 80 kDa, about 50 kDa to about 90 kDa, about 50 kDa to about 100 kDa, about 60 kDa to about 70 kDa, about 60 kDa to about 80 kDa, about 60 kDa to about 90 kDa, about 60 kDa to about 100 kDa, about 70 kDa to about 80 kDa, about 70 kDa to about 90 kDa, about 70 kDa to about 100 kDa, about 80 kDa to about 90 kDa, about 80 kDa to about 100 kDa, or about 90 kDa to about 100 kDa.

29. The method according to any one of embodiments 1-28, wherein the protein attached with the polysaccharide using a covalent linkage.

30. The method according to any one of embodiments 1-29, wherein the polysaccharide is attached to the protein by its reducing end terminal unit, its non-reducing terminal unit, or both.

31. The method according to any one of embodiments 1-30, wherein the population of the protein attached to the polysaccharide has a polydispersity of less than 1.3, less than 1.25, less than 1.2, less than 1.15, less than 1.1, or less than 1.05.

32. The method according to any one of embodiments 1-31, wherein the population of the protein attached to the polysaccharide has a polydispersity range of about 1.05 to about 1.3, about 1.05 to about 1.25, about 1.05 to about 1.2, about 1.05 to about 1.15, about 1.05 to about 1.1, about 1.1 to about 1.3, about 1.1 to about 1.25, about 1.1 to about 1.2, about 1.1 to about 1.15, about 1.15 to about 1.3, about 1.15 to about 1.25, or about 1.15 to about 1.2.

33. The method according to any one of embodiments 1-32, wherein the population substantially comprises only proteins having the polysaccharide attached to a N-terminus of the protein.

34. The method according to any one of embodiments 1-33, wherein the proteins having the polysaccharide attached to a N-terminus of the protein is about 70%, about 75%, about 80%, about 85%, about 90% or about 95% of the total proteins of the population.

35. The method according to any one of embodiments 1-33, wherein the proteins having the polysaccharide attached to a N-terminus of the protein is at least 70%, at least 75%, at least 80%, at least 85%, at least 90% or at least 95% of the total proteins of the population.

36. The method according to any one of embodiments 1-33, wherein the proteins having the polysaccharide attached to a N-terminus of the protein is at most 70%, at most 75%, at most 80%, at most 85%, at most 90% or at most 95% of the total proteins of the population.

37. The method according to any one of embodiments 1-33, wherein the proteins having the polysaccharide attached to a N-terminus of the protein is in a range of about 70% to about 75%, about 70% to about 80%, about 70% to about 85%, about 70% to about 90%, about 70% to about 95%, about 70% to about 96%, about 70% to about 97%, about 70% to about 98%, about 70% to about 99%, about 70% to about 100%, about 75% to about 80%, about 75% to about 85%, about 75% to about 90%, about 75% to about 95%, about 75% to about 96%, about 75% to about 97%, about 75% to about 98%, about 75% to about 99%, about 75% to about 100%, about 80% to about 85%, about 80% to about 90%, about 80% to about 95%, about 80% to about 96%, about 80% to about 97%, about 80% to about 98%, about 80% to about 99%, about 80% to about 100%, about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, or about 95% to about 100% of the total proteins of the population.

38. The method according to any one of embodiments 2-33, wherein the insulin protein or insulin-like protein is derivatized substantially only at the N-terminal of the B-chain of the insulin or insulin-like protein.

39. The method according to any one of embodiments 1-38, wherein the pharmaceutical composition further comprises one or more pharmaceutically acceptable excipients.

40. The method according to any one of embodiments 1-39, wherein the intranasal administration is through the nasal mucosa.

41. A method of treating a neurological disorder or a method of treating insulin resistance in an individual, the method comprising administering to the brain of the individual a pharmaceutical composition comprising a population of a protein attached with a polysaccharide.

42. Use of a pharmaceutical composition comprising a population of a protein attached with a polysaccharide in the manufacture of a medicament for the treatment of a neurological disorder or insulin resistance.

43. Use of a pharmaceutical composition comprising a population of a protein attached with a polysaccharide in treating a neurological disorder or insulin resistance.

44. Use of a pharmaceutical composition comprising a population of a protein attached with a polysaccharide in the manufacture of a medicament for the administration of a therapeutically effective amount of the protein to the brain of an individual 45. Use of a pharmaceutical composition comprising a population of a protein attached with a polysaccharide in administering a therapeutically effective amount of the protein to the brain of an individual 46. The method according to embodiment 41 or the use according to any one of embodiments 42-45, wherein the protein is an insulin and/or an insulin-like protein.

47. The method or use according to embodiment 46, wherein the insulin is a natural insulin derived from an animal or a synthetic insulin.

48. The method or use according to embodiment 47, wherein the natural insulin is derived from a human.

49. The method or use according to any one of embodiments 46-48, wherein the insulin comprised SEQ ID NO: 1, SEQ ID NO: 2, or SEQ ID NO: 3.

50. The method or use according to any one of embodiments 46-49, wherein the insulin-like protein is a homolog, paralog, or ortholog of insulin.

51. The method or use according to any one of embodiments 46-50, wherein the insulin-like protein has an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

52. The method or use according to any one of embodiments 46-51, wherein the insulin-like protein has an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

53. The method or use according to any one of embodiments 46-52, wherein the insulin-like protein has at least 1, at least 2, at least 3, at least 4, at least 5, at least 6, at least 7, at least 8, at least 9, at least 10, at least 11, at least 12, at least 13, at least 14, or at least 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

54. The method or use according to any one of embodiments 46-52, wherein the insulin-like protein has at most 1, at most 2, at most 3, at most 4, at most 5, at most 6, at most 7, at most 8, at most 9, at most 10, at most 11, at most 12, at most 13, at most 14, or at most 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

55. The method or use according to any one of embodiments 46-54, wherein the insulin-like protein has at least 1, at least 2, at least 3, at least 4, at least 5, at least 6, at least 7, at least 8, at least 9, at least 10, at least 11, at least 12, at least 13, at least 14, or at least 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8;

56. The method or use according to any one of embodiments 46-54, wherein the insulin-like protein has at most 1, at most 2, at most 3, at most 4, at most 5, at most 6, at most 7, at most 8, at most 9, at most 10, at most 11, at most 12, at most 13, at most 14, or at most 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

57. The method or use according to any one of embodiments 46-54, wherein the insulin-like protein comprises the A-chain/B-chain amino acid sequence combinations of SEQ ID NO: 3/SEQ ID NO: 4, or SEQ ID NO: 3/SEQ ID NO: 5, or SEQ ID NO: 3/SEQ ID NO: 6, or SEQ ID NO: 3/SEQ ID NO: 7, or SEQ ID NO: 3/SEQ ID NO: 8.

58. The method or use according to any one of embodiments 41-57, wherein the polysaccharide is an anionic polysaccharide.

59. The method or use according to any one of embodiments 41-58, wherein the anionic polysaccharide is a polysialic acid, a heparin, a hyaluronic acid and a chondroitin sulphate.

60. The method or use according to embodiment 59, wherein the polysialic acid is derived from a bacterial source or a mammalian source.

61. The method or use according to embodiment 60, wherein the bacterial source is a polysaccharide B of *E. coli* KI, *N. meningitidis, Maraxella liquefaciens* or *Pasteurella aeruginosa*, a K92 polysaccharide from *E. coli* K92 strain, or a C polysaccharides of *N. meningitides*.

62. The method or use according to any one of embodiments 59-61, wherein the polysialic acid is a homopolymeric form, a heteropolymeric form, or a co-polymer form.

63. The method or use according to any one of embodiments 58-62, wherein the anionic polysaccharide consists substantially only of sialic acid units.

64. The method or use according to any one of embodiments 58-62, wherein the anionic polysaccharide has both sialic acid units and saccharide units other than sialic acid in the molecule.

65. The method or use according to any one of embodiments 41-64, wherein the polysaccharide comprises about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 150, about 175, or about 200 saccharide units.

66. The method or use according to any one of embodiments 41-64, wherein the polysaccharide comprises at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 150, at least 175, or at least 200 saccharide units.

67. The method or use according to any one of embodiments 41-64, wherein the polysaccharide comprises about at most 2, at most 3, at most 4, at most 5, at most 6, at most 7, at most 8, at most 9, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95, at most 100, at most 105, at most 110, at most 115, at most 120, at most 125, at most 150, at most 175, or at most 200 saccharide units.

68. The method or use according to any one of embodiments 41-64, wherein the polysaccharide comprises about 2 to about 200, about 2 to about 175, about 2 to about 150, about 2 to about 125, about 2 to about 100, about 2 to about 90, about 2 to about 80, about 2 to about 75, about 2 to about 70, about 2 to about 60, about 2 to about 50, about 2 to about 40, about 2 to about 30, about 2 to about 25, about 2 to about 20, about 2 to about 15, about 2 to about 10, about 5 to about 200, about 5 to about 175, about 5 to about 150, about 5 to about 125, about 5 to about 100, about 5 to about 90, about 5 to about 80, about 5 to about 75, about 5 to about 70, about 5 to about 60, about 5 to about 50, about 5 to about 40, about 5 to about 30, about 5 to about 25, about 5 to about 20, about 5 to about 15, about 5 to about 10, about 10 to about 200, about 10 to about 175, about 10 to about 150, about 10 to about 125, about 10 to about 100, about 10 to about 90, about 10 to about 80, about 10 to about 75, about 10 to about 70, about 10 to about 60, about 10 to about 50, about 10 to about 40, about 10 to about 30, about 10 to about 25, about 10 to about 20, about 10 to about 15, about 20 to about 200, about 20 to about 175, about 20 to about 150, about 20 to about 100, about 20 to about 90, about 20 to about 80, about 20 to about 75, about 20 to about 70, about 20 to about 60, about 20 to about 50, about 20 to about 40, about 20 to about 30, about 30 to about 200, about 30 to about 175, about 30 to about 150, about 30 to about 100, about 30 to about 90, about 30 to about 80, about 30 to about 75, about 30 to about 70, about 30 to about 60, about 30 to about 50, about 30 to about 40, about 40 to about 200, about 40 to about 175, about 40 to about 150, about 40 to about 100, about 40 to about 90, about 40 to about 80, about 40 to about 75, about 40 to about 70, about 40 to about 60, about 40 to about 50, about 50 to about 200, about 50 to about 175, about 50 to about 150, about 50 to about 100, about 50 to about 90, about 50 to about 80, about 50 to about 75, about 50 to about 70, about 50 to about 60, about 60 to about 200, about 60 to about 175, about 60 to about 150, about 60 to about 100, about 60 to about 90, about 60 to about 80, about 60 to about 75, about 60 to about 70, about 70 to about 200, about 70 to about 175, about 70 to about 150, about 70 to about 100, about 70 to about 90, about 70 to about 80, about 70 to about 75, about 75 to about 200, about 75 to about 175, about 75 to about 150, about 75 to about 100, about 75 to about 90, about 75 to about 80, about 80 to about 200, about 80 to about 175, about 80 to about 150, about 80 to about 100, about 80 to about 90, about 90 to about 200, about 90 to about 175, about 90 to about 150, about 90 to about 100, about 100 to about 200, about 100 to about 175, about 100 to about 150, about 125 to about 200, about 125 to about 175, about 125 to about 150, about 150 to about 200, about 150 to about 175, or about 175 to about 200, saccharide units.

69. The method or use according to any one of embodiments 41-68, wherein the polysaccharide has a weight average molecular weight of about 1 kDa, about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa or about 100 kDa.

70. The method or use according to any one of embodiments 41-68, wherein the polysaccharide has a weight average molecular weight of at least 1 kDa, at least 2 kDa, at least 3 kDa, at least 4 kDa, at least 5 kDa, at least 6 kDa, at least 7 kDa, at least 8 kDa, at least 9 kDa, at least 10 kDa, at least 11 kDa, at least 12 kDa, at least 13 kDa, at least 14 kDa, at least 15 kDa, at least 16 kDa, at least 17 kDa, at least 18 kDa, at least 19 kDa, at least 20 kDa, at least 21 kDa, at least 22 kDa, at least 23 kDa, at least 24 kDa, at least 25 kDa, at least 26 kDa, at least 27 kDa, at least 28 kDa, at least 29 kDa, at least 30 kDa, at least 31 kDa, at least 32 kDa, at least 33 kDa, at least 34 kDa, at least 35 kDa, at least 40 kDa, at least 45 kDa, at least 50 kDa, at least 55 kDa, at least 60 kDa, at least 65 kDa, at least 70 kDa, at least 75 kDa, at least 80 kDa, at least 85 kDa, at least 90 kDa, at least 95 kDa or at least 100 kDa.

71. The method or use according to any one of embodiments 41-68, wherein the polysaccharide has a weight average molecular weight at most 1 kDa, at most 2 kDa, at most 3 kDa, at most 4 kDa, at most 5 kDa, at most 6 kDa, at most 7 kDa, at most 8 kDa, at most 9 kDa, at most 10 kDa, at most 11 kDa, at most 12 kDa, at most 13 kDa, at most 14 kDa, at most 15 kDa, at most 16 kDa, at most 17 kDa, at most 18 kDa, at most 19 kDa, at most 20 kDa, at most 21 kDa, at most 22 kDa, at most 23 kDa, at most 24 kDa, at most 25 kDa, at most 26 kDa, at most 27 kDa, at most 28 kDa, at most 29 kDa, at most 30 kDa, at most 31 kDa, at most 32 kDa, at most 33 kDa, at most 34 kDa, at most 35 kDa, at most 40 kDa, at most 45 kDa, at most 50 kDa, at most 55 kDa, at most 60 kDa, at most 65 kDa, at most 70 kDa, at most 75 kDa, at most 80 kDa, at most 85 kDa, at most 90 kDa, at most 95 kDa or at most 100 kDa.

72. The method or use according to any one of embodiments 41-68, wherein the polysaccharide has a weight average molecular weight in the range of about 2 kDa to about 10 kDa, about 2 kDa to about 15 kDa, about 2 kDa to about 20 kDa, about 2 kDa to about 25 kDa, about 2 kDa to about 30 kDa, about 2 kDa to about 35 kDa, about 2 kDa to about 40 kDa, about 2 kDa to about 45 kDa, about 2 kDa to about 50 kDa, about 2 kDa to about 60 kDa, about 2 kDa to about 70 kDa, about 2 kDa to about 80 kDa, about 2 kDa to about 90 kDa, about 2 kDa to about 100 kDa, about 5 kDa to about 10 kDa, about 5 kDa to about 15 kDa, about 5 kDa to about 20 kDa, about 5 kDa to about 25 kDa, about 5 kDa to about 30 kDa, about 5 kDa to about 35 kDa, about 5 kDa to about 40 kDa, about 5 kDa to about 45 kDa, about 5 kDa to about 50 kDa, about 5 kDa to about 60 kDa, about 5 kDa to about 70 kDa, about 5 kDa to about 80 kDa, about 5 kDa to about 90 kDa, about 5 kDa to about 100 kDa, about 10 kDa to about 15 kDa, about 10 kDa to about 20 kDa, about 10 kDa to about 25 kDa, about 10 kDa to about 30 kDa, about 10 kDa to about 35 kDa, about 10 kDa to about 40 kDa, about 10 kDa to about 45 kDa, about 10 kDa to about 50 kDa, about 10 kDa to about 60 kDa, about 10 kDa to about 70 kDa, about 10 kDa to about 80 kDa, about 10 kDa to about 90 kDa, about 10 kDa to about 100 kDa, about 15 kDa to about 20 kDa, about 15 kDa to about 25 kDa, about 15 kDa to about 30 kDa, about 15 kDa to about 35 kDa, about 15 kDa to about 40 kDa, about 15 kDa to about 45 kDa, about 15 kDa to about 50 kDa, about 15 kDa to about 60 kDa, about 15 kDa to about 70 kDa, about 15 kDa to about 80 kDa, about 15 kDa to about 90 kDa, about 15 kDa to about 100 kDa, about 20 kDa to about 25 kDa, about 20 kDa to about 30 kDa, about 20 kDa to about 35 kDa, about 20 kDa to about 40 kDa, about 20 kDa to about 45 kDa, about 20 kDa to about 50 kDa, about 20 kDa to about 60 kDa, about 20 kDa to about 70 kDa, about 20 kDa to about 80 kDa, about 20 kDa to about 90 kDa, about 20 kDa to about 100 kDa, about 25 kDa to about 30 kDa, about 25 kDa to about 35 kDa, about 25 kDa to about 40 kDa, about 25 kDa to about 45 kDa, about 25 kDa to about 50 kDa, about 25 kDa to about 60 kDa, about 25 kDa to about 70 kDa, about 25 kDa to about 80 kDa, about 25 kDa to about 90 kDa, about 25 kDa to about 100 kDa, about 30 kDa to about 35 kDa, about 30 kDa to about 40 kDa, about 30 kDa to about 45 kDa, about 30 kDa to about 50 kDa, about 30 kDa to about 60 kDa, about 30 kDa to about 70 kDa, about 30 kDa to about 80 kDa, about 30 kDa to about 90 kDa, about 30 kDa to about 100 kDa, about 35 kDa to about 40 kDa, about 35 kDa to about 45 kDa, about 35 kDa to about 50 kDa, about 35 kDa to about 60 kDa, about 35 kDa to about 70 kDa, about 35 kDa to about 80 kDa, about 35 kDa to about 90 kDa, about 35 kDa to about 100 kDa, about 40 kDa to about 45 kDa, about 40 kDa to about 50 kDa, about 40 kDa to about 60 kDa, about 40 kDa to about 70 kDa, about 40 kDa to about 80 kDa, about 40 kDa to about 90 kDa, about 40 kDa to about 100 kDa, about 45 kDa to about 50 kDa, about 45 kDa to about 60 kDa, about 45 kDa to about 70 kDa, about 45 kDa to about 80 kDa, about 45 kDa to about 90 kDa, about 45 kDa to about 100 kDa, about 50 kDa to about 60 kDa, about 50 kDa to about 70 kDa, about 50 kDa to about 80 kDa, about 50 kDa to about 90 kDa, about 50 kDa to about 100 kDa, about 60 kDa to about 70 kDa, about 60 kDa to about 80 kDa, about 60 kDa to about 90 kDa, about 60 kDa to about 100 kDa, about 70 kDa to about 80 kDa, about 70 kDa to about 90 kDa, about 70 kDa to about 100 kDa, about 80 kDa to about 90 kDa, about 80 kDa to about 100 kDa, or about 90 kDa to about 100 kDa.

73. The method or use according to any one of embodiments 41-72, wherein the protein attached with the polysaccharide using a covalent linkage.

74. The method or use according to any one of embodiments 41-73, wherein the polysaccharide is attached to the protein by its reducing end terminal unit, its non-reducing terminal unit, or both.

75. The method or use according to any one of embodiments 41-74, wherein the population of the protein attached to the polysaccharide has a polydispersity of less than 1.3, less than 1.25, less than 1.2, less than 1.15, less than 1.1, or less than 1.05.

76. The method or use according to any one of embodiments 41-75, wherein the population of the protein attached to the polysaccharide has a polydispersity range of about 1.05 to about 1.3, about 1.05 to about 1.25, about 1.05 to about 1.2, about 1.05 to about 1.15, about 1.05 to about 1.1, about 1.1 to about 1.3, about 1.1 to about 1.25, about 1.1 to about 1.2, about 1.1 to about 1.15, about 1.15 to about 1.3, about 1.15 to about 1.25, or about 1.15 to about 1.2.

77. The method or use according to any one of embodiments 41-76, wherein the population substantially comprises only proteins having the polysaccharide attached to a N-terminus of the protein.

78. The method or use according to any one of embodiments 41-77, wherein the proteins having the polysaccharide attached to a N-terminus of the protein is about 70%, about 75%, about 80%, about 85%, about 90% or about 95% of the total proteins of the population.

79. The method or use according to any one of embodiments 41-77, wherein the proteins having the polysaccharide attached to a N-terminus of the protein is at least 70%, at least 75%, at least 80%, at least 85%, at least 90% or at least 95% of the total proteins of the population.

80. The method or use according to any one of embodiments 41-77, wherein the proteins having the polysaccharide attached to a N-terminus of the protein is at most 70%, at most 75%, at most 80%, at most 85%, at most 90% or at most 95% of the total proteins of the population.

81. The method or use according to any one of embodiments 41-77, wherein the proteins having the polysaccharide attached to a N-terminus of the protein is in a range of about 70% to about 75%, about 70% to about 80%, about 70% to about 85%, about 70% to about 90%, about 70% to about 95%, about 70% to about 96%, about 70% to about 97%, about 70% to about 98%, about 70% to about 99%, about 70% to about 100%, about 75% to about 80%, about 75% to about 85%, about 75% to about 90%, about 75% to about 95%, about 75% to about 96%, about 75% to about 97%, about 75% to about 98%, about 75% to about 99%, about 75% to about 100%, about 80% to about 85%, about 80% to about 90%, about 80% to about 95%, about 80% to about 96%, about 80% to about 97%, about 80% to about 98%, about 80% to about 99%, about 80% to about 100%, about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, or about 95% to about 100% of the total proteins of the population.

82. The method or use according to any one of embodiments 41-81, wherein the insulin protein or insulin-like protein is derivatized substantially only at the N-terminal of the B-chain of the insulin or insulin-like protein.

83. The method or use according to any one of embodiments 41-82, wherein the pharmaceutical composition further comprises one or more pharmaceutically acceptable excipients.

84. The method or use according to any one of embodiments 41-83, wherein the intranasal administration is through the nasal mucosa.

85. The method or use according to any one of embodiments 41-43 or 46-84, wherein the neurological disorder is a memory disorder, a head injury, a spinal cord injury, a seizure, a stroke, a dementia, a memory loss, an attention deficit disorder (ADD), an epilepsy, an ischemia, a Amyotrophic Lateral Sclerosis (ALS), a multiple sclerosis, a Huntington's disease, a Parkinson's disease, a Alzheimer's disease, CNS damage resulting from infectious disease, CNS damage resulting from a tumor, a mood disorder, an anxiety disorder, a memory disorder, or a schizophrenic disorder.

86. The method or use according to embodiment 85, wherein the infectious disease is a viral encephalitis, a bacterial meningitis, or a viral meningitis.

87. The method or use according to embodiment 85, wherein the mood disorder is a depression or a bipolar disorder.

88. The method or use according to any one of embodiments 41-43 or 46-87, wherein the insulin resistance is associated with type-2 diabetes, obesity, systemic inflammation, chronic pancreatitis, hypertension, hyperglycycemia, dyslipidemia, promoting weight loss, gestational diabetes, colon cancer, prostate cancer, pancreatic cancer, or chronic liver disease.

89. The method or use according to any one of embodiments 41-43 or 46-87, wherein the insulin resistance is associated with type-2 diabetes.

90. A composition according to any of embodiments 1-89 for use in therapy.

91. A method for producing a polysaccharide derivative of an insulin-like protein, the method comprising the step of chemically reacted a polysaccharide substantially only at the N-terminal amine of the insulin-like protein.

92. The method according to embodiment 91, wherein the polysaccharide is an anionic polysaccharide.

93. The method according to embodiment 92, wherein the anionic polysaccharide is a polysialic acid, a heparin, a hyaluronic acid and a chondroitin sulphate.

94. The method according to embodiment 93, wherein the polysialic acid is derived from a bacterial source or a mammalian source.

95. The method according to embodiment 94, wherein the bacterial source is a polysaccharide B of *E. coli* KI, *N. meningitidis, Maraxella liquefaciens* or *Pasteurella aeruginosa*, a K92 polysaccharide from *E. coli* K92 strain, or a C polysaccharides of *N. meningitides*.

96. The method according to any one of embodiments 93-95, wherein the polysialic acid is a homopolymeric form, a heteropolymeric form, or a co-polymer form.

97. The method according to any one of embodiments 92-96, wherein the anionic polysaccharide consists substantially only of sialic acid units.

98. The method according to any one of embodiments 92-97, wherein the anionic polysaccharide has both sialic acid units and saccharide units other than sialic acid in the molecule.

99. The method according to any one of embodiments 91-98, wherein the polysaccharide comprises about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 150, about 175, or about 200 saccharide units.

100. The method according to any one of embodiments 91-98, wherein the polysaccharide comprises at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 150, at least 175, or at least 200 saccharide units.

101. The method according to any one of embodiments 91-98, wherein the polysaccharide comprises about at most 2, at most 3, at most 4, at most 5, at most 6, at most 7, at most 8, at most 9, at most 10, at most 15, at most 20, at most 25, at most 30, at most 35, at most 40, at most 45, at most 50, at most 55, at most 60, at most 65, at most 70, at most 75, at most 80, at most 85, at most 90, at most 95, at most 100, at most 105, at most 110, at most 115, at most 120, at most 125, at most 150, at most 175, or at most 200 saccharide units.

102. The method according to any one of embodiments 91-98, wherein the polysaccharide comprises about 2 to about 200, about 2 to about 175, about 2 to about 150, about 2 to about 125, about 2 to about 100, about 2 to about 90, about 2 to about 80, about 2 to about 75, about 2 to about 70, about 2 to about 60, about 2 to about 50, about 2 to about 40, about 2 to about 30, about 2 to about 25, about 2 to about 20, about 2 to about 15, about 2 to about 10, about 5 to about 200, about 5 to about 175, about 5 to about 150, about 5 to about 125, about 5 to about 100, about 5 to about 90, about 5 to about 80, about 5 to about 75, about 5 to about 70, about 5 to about 60, about 5 to about 50, about 5 to about 40, about 5 to about 30, about 5 to about 25, about 5 to about 20, about 5 to about 15, about 5 to about 10, about 10 to about 200, about 10 to about 175, about 10 to about 150, about 10 to about 125, about 10 to about 100, about 10 to about 90, about 10 to about 80, about 10 to about 75, about 10 to about 70, about 10 to about 60, about 10 to about 50, about 10 to about 40, about 10 to about 30, about 10 to about 25, about 10 to about 20, about 10 to about 15, about 20 to about 200, about 20 to about 175, about 20 to about 150, about 20 to about 100, about 20 to about 90, about 20 to about 80, about 20 to about 75, about 20 to about 70, about 20 to about 60, about 20 to about 50, about 20 to about 40, about 20 to about 30, about 30 to about 200, about 30 to about 175, about 30 to about 150, about 30 to about 100, about 30 to about 90, about 30 to about 80, about 30 to about 75, about 30 to about 70, about 30 to about 60, about 30 to about 50, about 30 to about 40, about 40 to about 200, about 40 to about 175, about 40 to about 150, about 40 to about 100, about 40 to about 90, about 40 to about 80, about 40 to about 75, about 40 to about 70, about 40 to about 60, about 40 to about 50, about 50 to about 200, about 50 to about 175, about 50 to about 150, about 50 to about 100, about 50 to about 90, about 50 to about 80, about 50 to about 75, about 50 to about 70, about 50 to about 60, about 60 to about 200, about 60 to about 175, about 60 to about 150, about 60 to about 100, about 60 to about 90, about 60 to about 80, about 60 to about 75, about 60 to about 70, about 70 to about 200, about 70 to about 175, about 70 to about 150, about 70 to about 100, about 70 to about 90, about 70 to about 80, about 70 to about 75, about 75 to about 200, about 75 to about 175, about 75 to about 150, about 75 to about 100, about 75 to about 90, about 75 to about 80, about 80 to about 200, about 80 to about 175, about 80 to about 150, about 80 to about 100, about 80 to about 90, about 90 to about 200, about 90 to about 175, about 90 to about 150, about 90 to about 100, about 100 to about 200, about 100 to about 175, about 100 to about 150, about 125 to about 200, about 125 to about 175, about 125 to about 150, about 150 to about 200, about 150 to about 175, or about 175 to about 200, saccharide units.

103. The method according to any one of embodiments 91-102, wherein the polysaccharide has a weight average molecular weight of about 1 kDa, about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa or about 100 kDa.

104. The method according to any one of embodiments 91-102, wherein the polysaccharide has a weight average molecular weight of at least 1 kDa, at least 2 kDa, at least 3 kDa, at least 4 kDa, at least 5 kDa, at least 6 kDa, at least 7 kDa, at least 8 kDa, at least 9 kDa, at least 10 kDa, at least 11 kDa, at least 12 kDa, at least 13 kDa, at least 14 kDa, at least 15 kDa, at least 16 kDa, at least 17 kDa, at least 18 kDa, at least 19 kDa, at least 20 kDa, at least 21 kDa, at least 22 kDa, at least 23 kDa, at least 24 kDa, at least 25 kDa, at least 26 kDa, at least 27 kDa, at least 28 kDa, at least 29 kDa, at least 30 kDa, at least 31 kDa, at least 32 kDa, at least 33 kDa, at least 34 kDa, at least 35 kDa, at least 40 kDa, at least 45 kDa, at least 50 kDa, at least 55 kDa, at least 60 kDa, at least 65 kDa, at least 70 kDa, at least 75 kDa, at least 80 kDa, at least 85 kDa, at least 90 kDa, at least 95 kDa or at least 100 kDa.

105. The method according to any one of embodiments 91-102, wherein the polysaccharide has a weight average molecular weight at most 1 kDa, at most 2 kDa, at most 3 kDa, at most 4 kDa, at most 5 kDa, at most 6 kDa, at most 7 kDa, at most 8 kDa, at most 9 kDa, at most 10 kDa, at most 11 kDa, at most 12 kDa, at most 13 kDa, at most 14 kDa, at most 15 kDa, at most 16 kDa, at most 17 kDa, at most 18 kDa, at most 19 kDa, at most 20 kDa, at most 21 kDa, at most 22 kDa, at most 23 kDa, at most 24 kDa, at most 25 kDa, at most 26 kDa, at most 27 kDa, at most 28 kDa, at most 29 kDa, at most 30 kDa, at most 31 kDa, at most 32 kDa, at most 33 kDa, at most 34 kDa, at most 35 kDa, at most 40 kDa, at most 45 kDa, at most 50 kDa, at most 55 kDa, at most 60 kDa, at most 65 kDa, at most 70 kDa, at most 75 kDa, at most 80 kDa, at most 85 kDa, at most 90 kDa, at most 95 kDa or at most 100 kDa.

106. The method according to any one of embodiments 91-102, wherein the polysaccharide has a weight average molecular weight in the range of about 2 kDa to about 10 kDa, about 2 kDa to about 15 kDa, about 2 kDa to about 20 kDa, about 2 kDa to about 25 kDa, about 2 kDa to about 30 kDa, about 2 kDa to about 35 kDa, about 2 kDa to about 40 kDa, about 2 kDa to about 45 kDa, about 2 kDa to about 50 kDa, about 2 kDa to about 60 kDa, about 2 kDa to about 70 kDa, about 2 kDa to about 80 kDa, about 2 kDa to about 90 kDa, about 2 kDa to about 100 kDa, about 5 kDa to about 10 kDa, about 5 kDa to about 15 kDa, about 5 kDa to about 20 kDa, about 5 kDa to about 25 kDa, about 5 kDa to about 30 kDa, about 5 kDa to about 35 kDa, about 5 kDa to about 40 kDa, about 5 kDa to about 45 kDa, about 5 kDa to about 50 kDa, about 5 kDa to about 60 kDa, about 5 kDa to about 70 kDa, about 5 kDa to about 80 kDa, about 5 kDa to about 90 kDa, about 5 kDa to about 100 kDa, about 10 kDa to about 15 kDa, about 10 kDa to about 20 kDa, about 10 kDa to about 25 kDa, about 10 kDa to about 30 kDa, about 10 kDa to about 35 kDa, about 10 kDa to about 40 kDa, about 10 kDa to about 45 kDa, about 10 kDa to about 50 kDa, about 10 kDa to about 60 kDa, about 10 kDa to about 70 kDa, about 10 kDa to about 80 kDa, about 10 kDa to about 90 kDa, about 10 kDa to about 100 kDa, about 15 kDa to about 20 kDa, about 15 kDa to about 25 kDa, about 15 kDa to about 30 kDa, about 15 kDa to about 35 kDa, about 15 kDa to about 40 kDa, about 15 kDa to about 45 kDa, about 15 kDa to about 50 kDa, about 15 kDa to about 60 kDa, about 15 kDa to about 70 kDa, about 15 kDa to about 80 kDa, about 15 kDa to about 90 kDa, about 15 kDa to about 100 kDa, about 20 kDa to about 25 kDa, about 20 kDa to about 30 kDa, about 20 kDa to about 35 kDa, about 20 kDa to about 40 kDa, about 20 kDa to about 45 kDa, about 20 kDa to about 50 kDa, about 20 kDa to about 60 kDa, about 20 kDa to about 70 kDa, about 20 kDa to about 80 kDa, about 20 kDa to about 90 kDa, about 20 kDa to about 100 kDa, about 25 kDa to about 30 kDa, about 25 kDa to about 35 kDa, about 25 kDa to about 40 kDa, about 25 kDa to about 45 kDa, about 25 kDa to about 50 kDa, about 25 kDa to about 60 kDa, about 25 kDa to about 70 kDa, about 25 kDa to about 80 kDa, about 25 kDa to about 90 kDa, about 25 kDa to about 100 kDa, about 30 kDa to about 35 kDa, about 30 kDa to about 40 kDa, about 30 kDa to about 45 kDa, about 30 kDa to about 50 kDa, about 30 kDa to about 60 kDa, about 30 kDa to about 70 kDa, about 30 kDa to about 80 kDa, about 30 kDa to about 90 kDa, about 30 kDa to about 100 kDa, about 35 kDa to about 40 kDa, about 35 kDa to about 45 kDa, about 35 kDa to about 50 kDa, about 35 kDa to about 60 kDa, about 35 kDa to about 70 kDa, about 35 kDa to about 80 kDa, about 35 kDa to about 90 kDa, about 35 kDa to about 100 kDa, about 40 kDa to about 45 kDa, about 40 kDa to about 50 kDa, about 40 kDa to about 60 kDa, about 40 kDa to about 70 kDa, about 40 kDa to about 80 kDa, about 40 kDa to about 90 kDa, about 40 kDa to about 100 kDa, about 45 kDa to about 50 kDa, about 45 kDa to about 60 kDa, about 45 kDa to about 70 kDa, about 45 kDa to about 80 kDa, about 45 kDa to about 90 kDa, about 45 kDa to about 100 kDa, about 50 kDa to about 60 kDa, about 50 kDa to about 70 kDa, about 50 kDa to about 80 kDa, about 50 kDa to about 90 kDa, about 50 kDa to about 100 kDa, about 60 kDa to about 70 kDa, about 60 kDa to about 80 kDa, about 60 kDa to about 90 kDa, about 60 kDa to about 100 kDa, about 70 kDa to about 80 kDa, about 70 kDa to about 90 kDa, about 70 kDa to about 100 kDa, about 80 kDa to about 90 kDa, about 80 kDa to about 100 kDa, or about 90 kDa to about 100 kDa.

107. The method according to any one of embodiments 91-106, wherein the insulin-like protein is attached with the polysaccharide using a covalent linkage.

108. The method according to any one of embodiments 91-107, wherein the polysaccharide is attached to the protein by its reducing end terminal unit, its non-reducing terminal unit, or both.

109. The method according to any one of embodiments 91-108, wherein the anionic polysaccharide has a reactive aldehyde group which reacts with the insulin-like protein and the derivatisation reaction is carried out under reducing conditions.

110. The method according to embodiment 109, wherein the reactive aldehyde group is at the non-reducing end of the polysaccharide.

111. The method according to embodiment 109, wherein the reactive aldehyde is at the reducing end of the polysaccharide and the non-reducing end has been passivated such that it does not react with the insulin-like protein.

112. The method according to any one of embodiments 91-111, wherein the anionic polysaccharide or reaction intermediate reacts with a terminal amine group of the insulin-like protein in a first aqueous solution of acidic pH; and the resultant polysaccharide derivative is purified in a second aqueous solution of higher pH than the first aqueous solution.

113. The method according to embodiment 112, wherein the pH of the first aqueous solution is in the range 4.0-6.0 and the pH of the second aqueous solution is in the range 6.5-8.5.

114. The method according to any one of embodiments 91-113, which is carried out in the presence of a formulation additive.

115. The method according to embodiment 114, wherein the formulation additive is selected from one or more buffers, stabilisers, surfactants, salts, polymers, metal ions, sugars, polyols or amino acids.

EXAMPLES

The following non-limiting examples are provided for illustrative purposes only in order to facilitate a more complete understanding of representative embodiments now contemplated. These examples should not be construed to limit any of the embodiments described in the present specification.

Example 1

Preparation of a Polysaccharide Derivatised Insulin

1. Activation of Colominic Acid (CA)

Sodium meta-periodate and molecular weight markers were obtained from Sigma Chemical Laboratory, UK. The colominic acids (CAs) used were from Camida, Ireland.

Freshly prepared 0.02 M sodium metaperiodate ($NaIO_4$) solution (8 fold molar excess) was mixed with CA at 20° C. and the reaction mixture was stirred magnetically for 15 min in the dark. A two-fold volume of ethylene glycol was then added to the reaction mixture to expend excess $NaIO_4$ and the mixture left to stir at 20° C. for a further 30 min. The oxidised colominic acid (CAO) was dialysed (3.5 KDa molecular weight cut off dialysis tubing) extensively (24 h) against a 0.01% ammonium carbonate buffer (pH 7.4) at 4° C. Ultrafiltration (over molecular weight cut off 3.5 kDa) was used to concentrate the CAO solution from the dialysis tubing. Following concentration to required volume, the filtrate was lyophilized and stored at −40° C. until further use. Alternatively, CAO was recovered from the reaction mixture by precipitation (twice) with ethanol.

2. Determination of the Oxidation State of CA and Derivatives

Qualitative estimation of the degree of colominic acid oxidation was carried out with 2,4 dinitrophenylhydrazine (2,4-DNPH), which yields sparingly soluble 2,4 dinitrophenyl-hydrazones on interaction with carbonyl compounds. Non-oxidised (CA)/oxidised (CAO) were added to the 2,4-DNPH reagent (1.0 ml), the solutions were shaken and then allowed to stand at 37° C. until a crystalline precipitate was observed (Shriner et. al., The Systematic Identification of Organic Compounds, 6th ed., Wiley, New York, 1980). The degree (quantitative) of CA oxidation was measured with a method (Park, J. T., Johnson, M. J., Journal of Biological Chemistry, 181 (1949) 149-151) based on the reduction of ferricyanide ions in alkaline solution to ferric ferrocyanide (Persian blue), which is then measured at 630 nm. In this instance, glucose was used as a standard.

3. Gel Permeation Chromatography

The integrity of the internal alpha-2,8 linked Neu5Ac residues post periodate treatment was analysed by gel permeation chromatography. Colominic acid samples (CA and CAO) were dissolved in $NaNO_3$ (0.2M), $CH_3CN$ (10%; 5 mg/ml) and were chromatographed on over 2×GMPWXL columns with detection by refractive index (GPC system: VE1121 GPC solvent pump, VE3580 RI detector and collation with Trisec 3 software (Viscotek Europe Ltd). Samples (5 mg/ml) were filtered over 0.45 µm nylon membrane and run at 0.7 cm/min with 0.2M $NaNO_3$ and $CH_3CN$ (10%) as the mobile phase. The chromatographs obtained for the oxidised (CAO) material was compared with that of native CA. It was found that oxidized and native CA exhibit almost identical elution profiles, with no evidence that the successive oxidation step give rise to significant fragmentation of the polymer chain.

4. Preparation of COA-Insulin Conjugates (N-Terminal Specific)

Insulin (5804 Da) was supplied as white solid. The insulin was dissolved by minimum 100 mM HCl, and then adjusted to the required the pH and placed on ice. The amount of CAO to be added for conjugation was calculated based on formula:

$$\text{Weight of } CAO = \frac{\text{Amount of protein (g)}}{\text{(MW of protein)}} \times (\text{MW of } CAO) \times (\text{Molar excess of } CAO)$$

Required amount of CAO was weighed out. CAO was solubilised in 10 mM NaOAc, pH 6.0 gently vortexed the mixture until all the CAO has dissolved and then either filtered into a new container to remove any aggregated/precipitated material. Required amount of insulin protein solution was added to the CAO solution to give a 7.5 molar excess (small scale) and 5 molar excess (large scale) of CAO and gently mixed by keeping the reaction mixture on a gentle shaker at 4±1° C. 100 mg/ml $NaCNBH_3$ solution was added in order to have 8 mg/ml in the final reaction mixture, gently mixed and pH of the final reaction mixture was checked, if necessary adjusted the pH to 6.0 with 0.5 M NaOH/HCl at 4±1° C. Finally, the volume of the reaction was adjusted using 10 mM NaOAc, pH 6.0 to give a protein concentration of 1 mg/ml in the reaction mixture. Tube was sealed and stirred at desired temperature (4±1° C.) for 24 hours. The reaction was stopped by an appropriate method (such as tris(hydroxymethyl)aminomethane buffer pH 7.4) samples were taken out for SDS-PAGE (using 18% Tris glycine gel) and SE-HPLC (Superose 12 column) and the reaction mixture checked and adjusted to pH 7.4 if necessary. To eliminate any precipitate the reaction mixture was centrifuged at 13000 rpm for 5 min before SE-HPLC analysis and/or purification. The data from peptide mapping and Edman degradation (FIG. 1) confirmed that the conjugate from pH 6.0 polysialation condition is N-terminally specifically blocked at the B chain of insulin. Specifically, the sequence G-I-V-E, identifies the A chain of insulin. The absence of amino acid Phe/Val/Asn/Gln indicated that the B chain of insulin was N-terminally blocked.

5. Purification and Characterization of CAO-Insulin Conjugates

Figure 2:
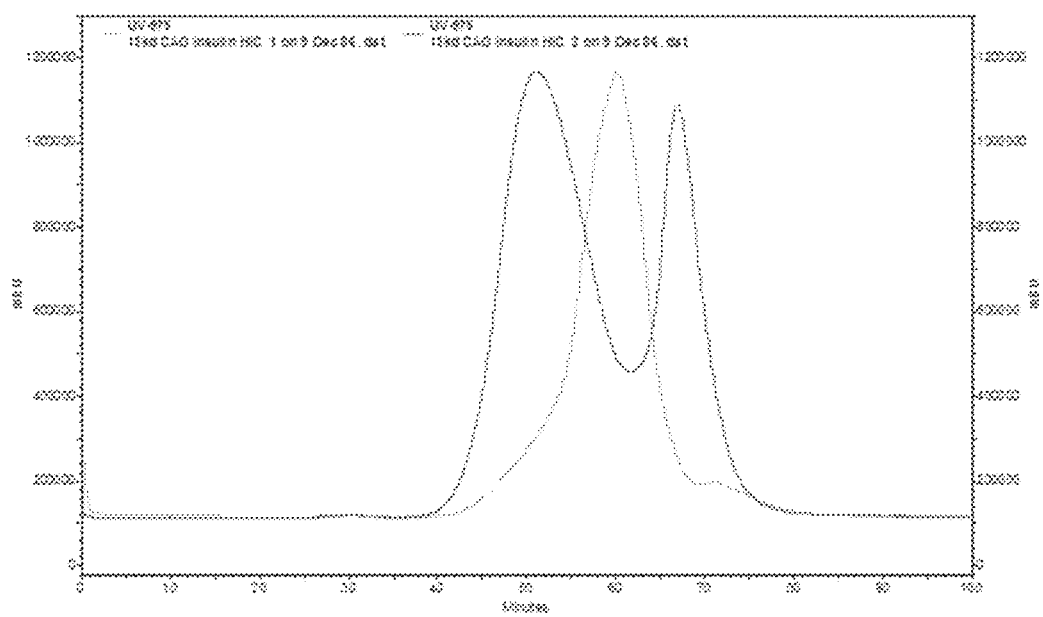
FIG. 2 shows the purification of a CAO-insulin conjugate by Hydrophobic Interaction Chromatography over a HiTrap Butyl FF column.

To remove free CAO from the mixture, Hydrophobic Interaction Chromatography (HIC) was used. Loading solution was prepared by diluting the insulin reaction mixture with minimum volume using concentrated $(NH_4)_2SO_4$ e.g. 3 M), 20 mM $Na_2HPO_4$, (pH 7.4) to give a concentration of 0.8 M $(NH_4)_2SO_4$ in the loading solution. The pH was adjusted to 7.4 with 0.5 M HCl/NaOH, the loading solution filtered using a 0.2 mm membrane filter. This solution is then loaded onto the HIC column (rate=0.5 ml/min) previously equilibrated with HIC buffer B (20 mM sodium phosphate+ 0.8 M $(NH_4)_2SO_4$, pH 7.4). Eluted fractions (each fraction 1.5 column volume) were collected and labeled (L1-Lx). The column was washed with HIC buffer B (at least 5 column volumes; rate=0.5 ml/min; collect 1.5 column volume fraction) and fractions collected and labeled (W1-Wx). The product was eluted with HIC buffer A (10 mM sodium phosphate buffer, pH 7.4) (rate=5 ml/min) and fractions collected (1 column volume fraction; 6 column volume) and labeled (E1-Ex). If two consecutive fractions were absent in protein content (UV280 nm), the next step was carried out. The samples were kept on ice during purification. The HIC effectively removes the free CA from the conjugated product (FIG. 2). The protein concentration was analysed by UV (280 nm) (Extinction coefficient of 1 mg/ml of insulin was about 1.043 at 280 nm). Samples were taken for SDS-PAGE and SE-HPLC.

The HIC protein-containing fractions are loaded onto an Ion Exchange Chromatography (IEC) column previously equilibrated with buffer A (20 mM phosphate buffer, pH 7.4). The product is eluted using a gradient comprising buffer A and buffer B (20 mM phosphate buffer+1M NaCl, pH 7.4) as follows: Buffer A: 90% buffer B 10%, 5CV & wash of 3CV, flow rate: 0.25 ml/min; Buffer A: 68%, buffer B: 32%, 5 CV & washing of 3CV, flow rate: 0.25 ml/min; Buffer A: 35%, buffer B: 65%, 5CV & washing of 3CV, flow rate: 0.25 ml/min; and Buffer A: 0%, buffer B: 100%, 5CV & washing of 3CV, flow rate: 0.25 ml/min.

Figure 3:
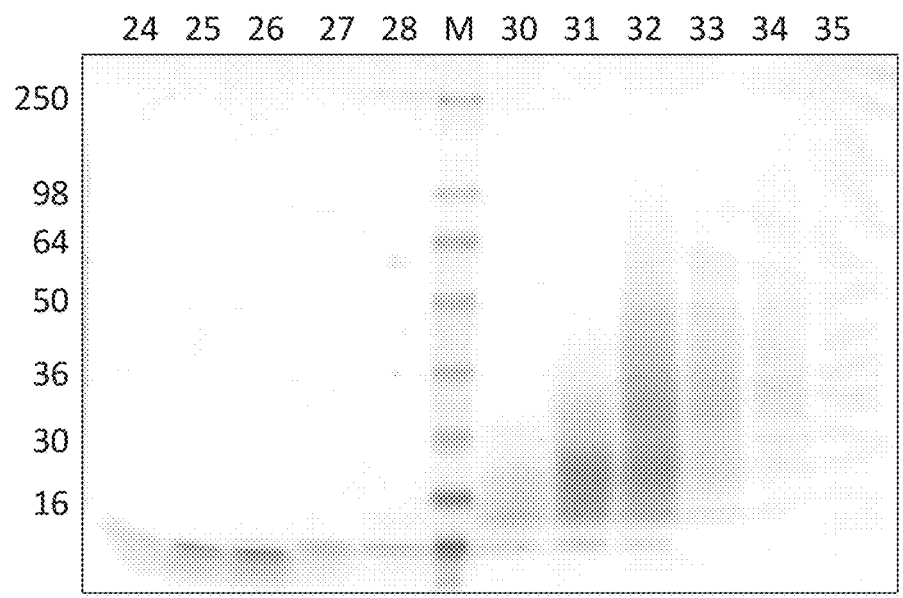
FIG. 3 shows the purification of a CAO-insulin conjugate from HIC peak 2, with 13 kDa CAO as example, by anion exchange chromatography over a Hitrap Q FF column. Molecular weight marker size is in KDa.

The IEC fractions containing the purified conjugate are combined, washed to remove salt with buffer change of PBS buffer. The pH is adjusted after removing salt to 7.4. The solution is then concentrated at 4±1° C. and the protein concentration analysed by UV spectroscopy (280 nm). Conjugates were sterile filtered and samples taken for activity assay and for characterisation by SDS-PAGE and SE-HPLC. If required an aliquot was removed for a protein assay and CA assay. The remainder was stored at 4±1° C. until further use and studied for physical stability by SE-HPLC. The effects of various processes affecting the stability of insulin in solution and the degree of derivatization were studied. The IEC results in the effective removal of insulin (FIG. 3).

6. SDS Polyacrylamide Gel Electrophoresis & Western Blotting

Figure 4:
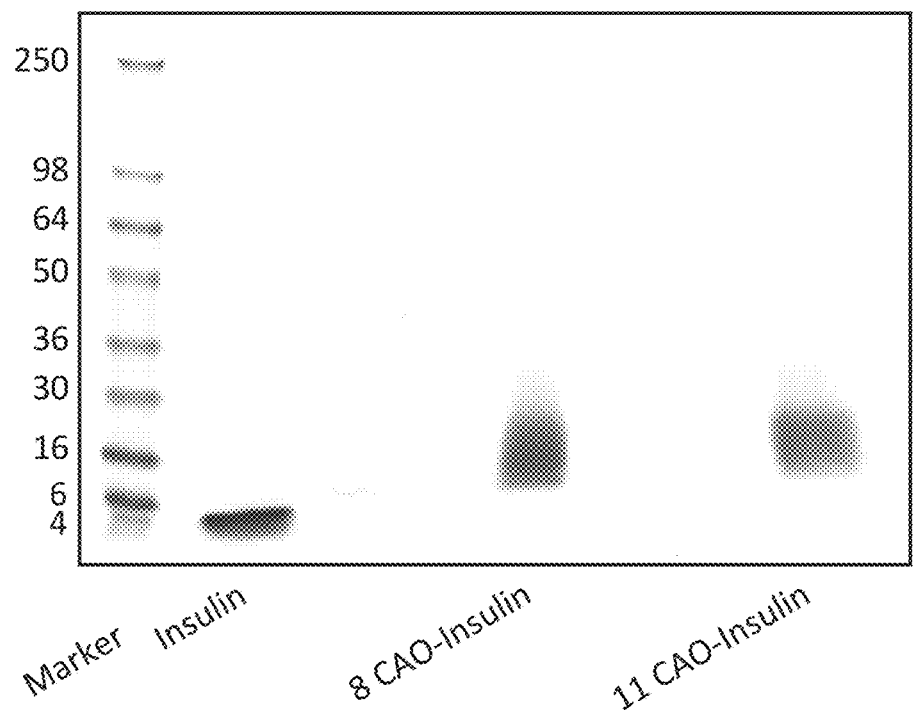
FIG. 4 is an SDS-PAGE of 8 kDa and 11 kDa CAO-rh-Insulin conjugates. Molecular weight marker size is in KDa.

SDS-PAGE was performed using 18% triglyine gels. Samples were diluted with either reducing or non reducing buffer and 5.0 µg of protein was loaded into each well. The gels were run on a triglycerine buffer system and was stained with Coomasie Blue (FIG. 4). Western blotting was performed using anti-PSA antibody.

Example 2

A Pilot Single Intranasal Dose of Sialong and Insulin in Mice

In this Example, the intranasal (IN) delivery of Sialong$^{AF647}$ and insulin$^{AF647}$ (described below) was evaluated to allow for adjustment of dose concentration and sample collection time point in the biodistribution study described in Example 3.

1. Preparation of the CAO-Insulin (Sialong) and Insulin Samples

Using the method set forth in Example 1, a polysialyated insulin conjugate was produced by N-terminal (B-chain) aldehyde conjugation (reductive amination) using 15 kDa CAO (24 mg/mL), insulin (4 mg/mL), 100 mM sodium phosphate, at pH 6.2, at 37° C. for 3 hours. After purification as described above, there was a 60% insulin yield. The resultant CAO-insulin had a molecular weight of 14.5 kDa and with an apparent pH of 7.35-7.45 in water. The purified product, referred to hereinafter as Sialong, was formulated as a pharmaceutical composition comprising m-cresol, and sodium phosphate (monosubstituted dehydrate) and sodium phosphate (di-substituted dehydrate) and 40 IU insulin. Human insulin (40 IU) is available as a commercial product and was formulated in an isotonic phosphate buffer saline.

The Sialong and human insulin were labeled with a fluorochrome, Alexa Flour (AF)-647 (Life Technologies/Thermal Fisher) using the commercial protocol. Each AF-647 labeled protein was evaluated for the degree of labeling based on the following calculations: Mole AF-647 dye per mole protein (A650×dilution factor)/(239,000×protein concentration, M), where 239,000 is an estimated molar extinction coefficient of the AF-647 dye at 650 nm.

To evaluate the purity of the AF-647-labeled Sialong and AF-647-labeled human insulin dose materials, an HPLC/UV diode-array was implemented to detect and to quantitate the chromatographic purity of the two labeled proteins. The labeled Sialong, Sialong$^{AF647}$, and labeled human insulin, insulin$^{AF647}$, were formulated in isotonic phosphate buffer saline which also contained m-cresol as a preservative, at pH 7.4, for intranasal delivery in anesthetized CD-1 mice.

Sialong$^{AF647}$ and insulin$^{AF647}$ concentrations in the dose formulation vehicles were assayed by a Bradford spectroscopic protein assay using the corresponding Sialong or human insulin protein as assay calibration.

2. Procedures—In-life Phase

Sialong$^{AF647}$ and insulin$^{AF647}$ were prepared and characterizations are presented in Table 1.

TABLE 1

| | Conjugation for Pilot Dosing | | | |
|---|---|---|---|---|
| Test Article | Degree of Labeling (DOL) | Dose Concentration (mg/mL) | Dose (mg/kg) | Dose Volume (µL/20 g body weight) |
| Insulin$^{AF647}$ | 1.0* | 2.40 | 0.6 | 5 |
| | | 12.0 | 3.0 | 5 |
| Sialong$^{AF647}$ | 1.1* | 8.40 | 2.1 | 5 |
| | | 42.0 | 10.5 | 5 |

*Slightly lower DOL was observed compared to previous conjugations; however, this has minimal impact as the brain assay sensitivity achieved by these conjugates was predicted to be sufficient for quantitation purposes.

Male CD-1 mice of 8 to 9 weeks of age (18-20 g body weight) were acclimatized for 7 days before being enrolled into the study. Mice were weighed and dosed at 5 µL of dosing material per 20 g of body weight. Mice were dosed at the originally proposed 1.5 mg/kg Sialong and 0.6 mg/kg insulin, as well as the increased doses of 7.5 mg/kg Sialong and 3.0 mg/kg insulin. Plasma, brain, lung, liver, kidney, and spleen samples were collected at nominal 10 minutes post-dose and assayed. Animals were anesthetized and held with the dorsal end facing down. Dosing materials were administered at a rate of ~1 µL/10 seconds split equally through both nostrils. Total dosing time ranged from 1.8 to 2.3 minutes.

After a nominal 10 minutes post-dose, animals were sacrificed followed by blood collection, perfusion, and tissue collection. The olfactory bulbs were included in the collection of the brain tissues. All tissues were stored at nominal −80° C. until assay. Perfusate contains: 1×PBS pH 7.4, +2.7% w/v BSA+100 U/mL heparin.

3. Procedures—Bioanalytical Phase

Brain—the optimal brain assay method—an acidified ethanol extraction followed by 4 hours of tandem enzyme digest—was successfully qualified and used for the quantitation of insulin$^{AF647}$ and sialong$^{AF647}$ in the brain in this pilot dosing study. Briefly, the procedures are outlined below:

Assay Day 1
1. Spike empty tubes with insulin/sialong-AF647 working stock or vehicle for test samples
2. Homogenized brains 10% w/v with ice-cold 0.1 mM HCl diH2O:Ethanol (25:75); the ENTIRE test sample brains were homogenized
3. Transferred 0.5 mL of blank brain homogenates to tubes from step 1 for preparation of calibration standards. Transferred 0.5 mL of each test sample into tubes from step 1. Assayed all test samples and calibration standards in duplicates
4. Shake overnight at 4° C. (~17.5 h) on orbital shaker.

Assay Day 2
5. Centrifuge all samples at 3500×g for 20 min at 4° C.
6. Collect 0.4 mL of supernatant for each sample
7. Evaporate until complete dryness under airflow of ~7 psi for ~70 min at 37° C.
8. Reconstitute all samples with reaction buffer containing 50 mM Tris pH 8 and 2 mM CaCl2
9. Add 1 U of proteinase K to all samples; invert mix well
10. Incubate all samples at 37° C. for 2 h
11. Mix samples well and adjust to ~pH 4 with citric acid; mix well
12. Add 1280 U of pepsin to all samples; invert mix well
13. Incubate all samples at 37° C. for 2 h
14. Vortex mix all samples and sonicate at RT
15. Centrifuge at 13200 rpm for 10 min at RT
16. Transfer 250 µL of supernatant of each sample onto 96-well plate
17. Take readings at Ex/Em of 635/675 nm Plasma—Briefly, the procedures are outlined below:
1. Spike empty tubes with insulin/sialong$^{AF647}$ working stock or vehicle for test samples
2. Added 200 µL of blank CD-1 mouse plasma K2EDTA to calibration standards; added 200 µL of test samples
3. Transferred to 96-well plate.
4. Read plate at Ex/Em 635/675.

Lung/Liver/Kidney/Spleen. Due to a lack of available blank CD-1 mouse tissue matrices available for calibration, BALB-c matrices were used as calibration models to quantify insulin/Sialong levels in CD-1 tissues.

To evaluate recovery and matrix differences between the calibration matrices and study test samples, a spiking recovery experiment was performed (Table 2). Based on these results, a correction factor was applied to the responses generated from the test sample assays prior to quantitation. The RFU correction factor was determined by dividing the response of each analyte spiked into BALB-c lysates (preparation procedures described below) by the response of each analyte spiked into CD-1 homogenate and then extracted. For kidney and liver matrices, there was enough material available to evaluate spiking recovery at two different levels. Hence, analyte response corrections from test samples were made based on extrapolation/interpolation against 2-point correction lines. However, due to lack of tissue material, lung and spleen spiking recovery tests could only be performed at one concentration level. Consequently, response corrections were made based on singular values.

TABLE 2

| Insulin | Conc Level (ng/g) | RFU correction factor | Sialong | Conc Level (ng/g) | RFU correction factor |
|---|---|---|---|---|---|
| Kidney | 150 | 1.26 | Kidney | 525 | 0.64 |
|  | 2000 | 0.94 |  | 7002 | 0.95 |
| Liver | 150 | 0.97 | Liver | 525 | 1.03 |
|  | 2000 | 0.98 |  | 7002 | 1.00 |
| Lung | 150 | 0.40 | Lung | 525 | 0.42 |
| Spleen | 150 | 0.76 | Spleen | 525 | 1.36 |

Briefly, the sample preparation procedures are outlined below: Homogenize blank and test sample tissues with a Polytron homogenizer with 10 parts (10% w/v) lysis buffer containing: 150 mM NaCl, 1 mM EDTA, 0.1% (w/v) SDS, 10 mM Sodium Phosphate, 1% (v/v) Triton X-100, adjusted to pH 7.1. For liver, due to the large size of this organ, a 1:1 tissue:lysis buffer ratio was used during homogenization.

1. Add remaining 9 parts of lysis buffer to liver homogenates
2. Lyse homogenates with 5 mm stainless steel beads with TissueLyzer by agitation at 25 Hz for 30 min
3. Further incubate lysates at RT for 30 min on orbital shaker
4. Pool lysates
5. Spike empty eppendorf tubes with insulin/sialong-AF647 working stock or vehicle for test samples
6. Centrifuge samples at 13200 rpm for 10 min to pellet debris
7. Transfer 250 µL of supernatant onto 96-well plate
8. Read plate at Ex/Em 635/675

4. Assay Performances

As depicted in Tables 3 and 4 which present the distribution of, insulin and Sialong, respectfully, calibration performances in all matrices were satisfactory and well within the typical bioanalytical acceptance criteria applied to bioassays of protein molecules of "20/25" (20% bias at all levels except at LLOQ, 25% bias).

TABLE 3

| Biodistribution of Insulin in Various Organs ||||||||
| Brain ||| Plasma ||| Lung |||
| Expected Conc. (ng/g) | Observed Conc. (ng/g) | % Bias | Expected Conc. (ng/mL) | Observed Conc. (ng/mL) | % Bias | Expected Conc. (ng/g) | Observed Conc. (ng/g) | % Bias |
|---|---|---|---|---|---|---|---|---|
| 10.0 | 11.0 | 9.9 | 1.80 | 1.43 | −20.4 | — | — | — |
|  | 9.64 | −3.6 |  | 1.98 | 10.1 | — | — | — |
| 20.0 | *29.4 | *47.0 | 12.0 | 8.97* | — | — | — | — |
|  | 16.7 | −16.4 |  | 11.8 | −2.0 | — | — | — |

TABLE 3-continued

Biodistribution of Insulin in Various Organs

| Expected Conc. (ng/g) | Observed Conc. (ng/g) | % Bias | Expected Conc. (ng/mL) | Observed Conc. (ng/mL) | % Bias | Expected Conc. (ng/g) | Observed Conc. (ng/g) | % Bias |
|---|---|---|---|---|---|---|---|---|
| 45.0 | 49.2 | 9.4 | 100 | 95.7 | -4.3 | — | — | — |
| — | 44.2 | -1.7 | — | 100 | 0.0 | 75.0 | 71.5 | -4.7 |
| 75.0 | 68.4 | -8.8 | 700 | 665 | -5.0 | 150 | 156 | 4.0 |
| — | 77.4 | 3.3 | — | 675 | -3.6 | 800 | 740 | -7.5 |
| 100 | 101.0 | 1.0 | 5000 | 5750 | 15.0 | 2000 | 2130 | 6.5 |
| — | 108.6 | 8.6 | — | 5750 | 15.0 | 10000 | 9900 | -1.0 |
| 200 | 199.8 | -0.1 | 30000 | 28500 | -5.0 | 35000 | 36100 | 3.1 |
| — | 194.9 | -2.5 | — | 30100 | 0.2 | 200000 | 199000 | -0.5 |
| Regression Method | Quadratic | | | Linear | | | Linear | |
| Weighting | $1/X^2$ | | | $1/X$ | | | $1/X$ | |

| Kidney | | Liver | | Spleen | |
|---|---|---|---|---|---|
| Observed Conc. (ng/g) | % Bias | Observed Conc. (ng/g) | % Bias | Observed Conc. (ng/g) | % Bias |
| — | — | — | — | — | — |
| — | — | — | — | — | — |
| — | — | — | — | — | — |
| — | — | — | — | — | — |
| — | — | — | — | — | — |
| 80.5 | 7.3 | 80.4 | 7.2 | 85.6 | 14.1 |
| 154 | 2.7 | 164 | 9.3 | 138 | -8.0 |
| 738 | -7.8 | 763 | -4.6 | 734 | -8.3 |
| 1980 | -1.0 | 1790 | -10.5 | 1970 | -1.5 |
| 9480 | -5.2 | 9710 | -2.9 | 10200 | 2.0 |
| 36500 | 4.3 | 35600 | 1.7 | 35900 | 2.6 |
| 199000 | -0.5 | 200000 | 0.0 | 199000 | -0.5 |
| Linear | | Quadratic | | Linear | |
| $1/X$ | | $1/X$ | | $1/X$ | |
| 0.9996 | | 0.9998 | | 0.9998 | |

TABLE 4

Biodistribution of Sialong in Various Organs

| Brain | | | Plasma | | | Lung | | |
|---|---|---|---|---|---|---|---|---|
| Expected Conc. (ng/g) | Observed Conc. (ng/g) | % Bias | Expected Conc. (ng/mL) | Observed Conc. (ng/mL) | % Bias | Expected Conc. (ng/g) | Observed Conc. (ng/g) | % Bias |
| — | — | — | 2.24 | 2.17 | -3.0 | — | — | — |
| — | — | — | — | 2.62 | 16.7 | — | — | — |
| — | — | — | 6.30 | 5.70 | -9.5 | — | — | — |
| — | — | — | — | 6.58 | 4.5 | — | — | — |
| — | — | — | 42.0 | 40.1 | -4.8 | — | — | — |
| — | — | — | — | 42.2 | 0.4 | — | — | — |
| — | — | — | 350 | 342 | -2.5 | 70.0 | 73.4 | 4.8 |
| — | — | — | — | 356 | 1.8 | 263 | 266 | 1.1 |
| — | — | — | 2451 | 2381 | -2.9 | 525 | 494 | -5.9 |
| — | — | — | — | 2414 | -1.5 | 2801 | 2745 | -2.0 |
| 157 | 158 | 0.6 | 17507 | 17646 | 0.7 | 7002 | 7142 | 2.0 |
| 262 | 257 | -1.8 | — | 17506 | 0.0 | 35012 | 35012 | 0.0 |
| 350 | 355 | 1.3 | 105043 | 105596 | 0.5 | 122542 | 122542 | 0.0 |
| 699 | 698 | -0.1 | — | 104476 | -0.5 | 700241 | 700241 | 0.0 |
| Regression Method | Quadratic | | | Quadratic | | | Quadratic | |
| Weighting | $1/X^2$ | | | $1/X$ | | | $1/X$ | |
| $R^2$ | 0.9996 | | | 1.0000 | | | 1.0000 | |

| Kidney | | Liver | | Spleen | |
|---|---|---|---|---|---|
| Observed Conc. (ng/g) | % Bias | Observed Conc. (ng/g) | % Bias | Observed Conc. (ng/g) | % Bias |
| — | — | — | — | — | — |
| — | — | — | — | — | — |
| — | — | — | — | — | — |
| — | — | — | — | — | — |
| — | — | — | — | — | — |
| — | — | — | — | — | — |
| 76.9 | 9.8 | — | — | 78.4 | 12.0 |
| 248 | -5.9 | 273 | 3.7 | 245 | -6.9 |

TABLE 4-continued

Biodistribution of Sialong in Various Organs

| 499 | −5.1 | 521 | −0.8 | 507 | −3.5 |
| 2815 | 0.5 | 2717 | −3.0 | 2759 | −1.5 |
| 7016 | 0.2 | 6988 | −0.2 | 7058 | 0.8 |
| 35152 | 0.4 | 35012 | 0.0 | 34452 | −1.6 |
| 122262 | −0.2 | 122542 | 0.0 | 123102 | 0.5 |
| 700241 | 0.0 | 700241 | 0.0 | 700241 | 0.0 |
| Quadratic | | Quadratic | | Quadratic | |
| 1/X | | 1/X | | 1/X | |
| 1.0000 | | 1.0000 | | 1.0000 | |

As depicted in Table 5, at equilmolar levels of dosed insulin, low levels of insulin were observed at both low dose (0.6 mg/kg) and high dose (3.0 mg/kg) levels. In addition, high variability was observed between animals of the same dose groups. The lower brain absorption of insulin compared to Sialong (Table 6) plus the low number of test animals may just have mathematically amplified the inter-animal variability. The high variability between replicates observed in animal 5 may be due to the less perfused brain for this animal causing interference in the detection of insulin. Generally, there appears to be an increase in systemic absorption of insulin when dose was increased without any increase in brain levels and undetectable levels in other tissues.

TABLE 5

Biodistribution of Insulin in Various Organs

| | | Plasma | | Brain | | Lung | | Kidney | | Liver | | Spleen | |
|---|---|---|---|---|---|---|---|---|---|---|---|---|---|
| Animal | Replicate | Conc. (ng/mL) | % Dose | Conc. (ng/g) | % Dose | Conc. (ng/g) | % Dose | Conc. (ng/g) | % Dose | Conc. (ng/g) | % Dose | Conc. (ng/g) | % Dose |
| Low Dose 1 | 1 | 14.4 | 0.04 | 4.99 | 0.02 | <LLOQ | — | <LLOQ | — | <LLOQ | — | <LLOQ | — |
|  | 2 | | | 22.5 | | | | | | | | | |
| Low Dose 2 | 1 | 11.8 | 0.04 | 11.3 | 0.02 | <LLOQ | — | <LLOQ | — | <LLOQ | — | <LLOQ | — |
|  | 2 | | | 9.87 | | | | | | | | | |
| High Dose 1 | 1 | 52.5 | 0.04 | 80.1 | 0.03 | <LLOQ | — | <LLOQ | — | <LLOQ | — | <LLOQ | — |
|  | 2 | | | 82.0 | | | | | | | | | |
| High Dose 2 | 1 | 39.6 | 0.03 | 7.52 | 0.00 | <LLOQ | — | <LLOQ | — | <LLOQ | — | <LLOQ | — |
|  | 2 | | | 7.15 | | | | | | | | | |

As depicted in Table 6, in brain, high levels of Sialong were detected at nominal 10 minutes post-dose at both low dose (2.1 mg/kg) and high dose (10.5 mg/kg) levels. Dose linearity of Sialong was observed. The results were reproducible between replicates with no more than (NMT) 10% CV. Sialong levels between animals of the same dose groups were comparable. Sialong were generally detected in lung and spleen tissues, following IN administration of high dose. However, there appeared to be some variability between animals as no Sialong was detected in lung tissue from High Dose Animal 1. Despite increasing dosage by a factor of 5, plasma and brain levels did not increase by the same amounts, possibly indicating saturation of absorption.

TABLE 6

Biodistribution of Sialong in Various Organs

| | | Plasma | | Brain | | Lung | | Kidney | | Liver | | Spleen | |
|---|---|---|---|---|---|---|---|---|---|---|---|---|---|
| Animal | Replicate | Conc. (ng/mL) | % Dose | Conc. (ng/g) | % Dose | Conc. (ng/g) | % Dose | Conc. (ng/g) | % Dose | Conc. (ng/g) | % Dose | Conc. (ng/g) | % Dose |
| Low Dose 1 | 1 | 45.4 | 0.0 | 891 | 0.47 | <LLOQ | — | <LLOQ | — | <LLOQ | — | <LLOQ | — |
|  | 2 | | | 903 | | | | | | | | | |
| Low Dose 2 | 1 | 42.0 | 0.0 | 630 | 0.32 | <LLOQ | — | <LLOQ | — | <LLOQ | — | <LLOQ | — |
|  | 2 | | | 578 | | | | | | | | | |
| High Dose 1 | 1 | 35.9 | 0.01 | 1377 | 0.13 | <LLOQ | — | <LLOQ | — | <LLOQ | — | 563 | 0.02 |
|  | 2 | | | 1231 | | | | | | | | | |
| High Dose 2 | 1 | 54.6 | 0.01 | 884 | 0.09 | 308 | 0.01 | <LLOQ | — | <LLOQ | — | 196 | 0.00 |
|  | 2 | | | 973 | | | | | | | | | |

Both Sialong and insulin were able to be detected 10 minutes post-dose in the brain. High concentration levels of Sialong were able to be detected in the mouse brain at both dose levels. Low concentration levels (close to assay lower limit of detection) of insulin was detected in the mouse brain even at the 3.0 mg/kg dose level, potentially due to the lower brain absorption of insulin compared to Sialong.

Sialong: As the dose increased from 2.1 to 10.5 mg/kg, these was a non-linear relationship between the Sialong brain and plasma levels. The tissue distribution values at 10.5 mg/kg were not much different from 2.1 mg/kg suggesting a possible saturation of the nasal mucosal surface for the delivery of Sialong.

Insulin: As the dose increased from 0.6 to 3.0 mg/kg, there was a linear relationship between the insulin brain and plasma levels.

Based on these results, a higher dose level than the initially proposed 0.6 mg/kg insulin and 1.5 mg/kg Sialong will provide the best chances to numerically compared plasma and brain levels across multiple timepoints. This dosing procedure is planned to be used during the main study due to its efficiency and minimization of dosing solution loss due to animals' "sneezing".

Example 3

Pharmacokinetics and Biodistribution of PSA-Insulin Following Intranasal Delivery in CD-1 Mice—Study 2

In this Example, a mouse biodistribution study is designed and performed to provide tissue concentration data on a CAO-insulin conjugate of the present invention following a single intranasal dose of the conjugate in CD-1 mice. Non-derivatised human insulin is also evaluated in the study.

1. Preparation of the CAO-Insulin and Insulin Samples

The AF-647 labeled Sialong, Sialong$^{AF647}$, and AF-647 labeled insulin, insulin$^{AF647}$, samples were prepared as described in Example 2.

Sialong$^{AF647}$ and insulin$^{AF647}$ concentrations in the dose formulation vehicles were assayed by a Bradford spectroscopic protein assay using the corresponding Sialong or human insulin protein as assay calibration. Characterizations are presented in Table 7.

TABLE 7

| Test Article | Degree of Labeling (DOL) | Protein MW (Unlabeled) Da | Dose Concentration mg/mL | Dose Level mg/kg | μmol insulin/kg |
|---|---|---|---|---|---|
| Insulin$^{AF647}$ | 1.5 | 5807 | 3.6 | 0.90 | 0.155 |
| Sialong$^{AF647}$ | 1.1 | 20307 | 12.6 | 3.15 | 0.155 |

2. Experimental Design

Male CD-1 mice of 8 to 9 weeks of age (18-20 g body weight) will be acclimatized for 7 days before being enrolled into the study. Insulin$^{AF647}$ and Sialong$^{AF647}$ were prepared as described above and their characterizations are presented below.

Animals were weighed and dosed at 5 μL of dosing material per 20 g of body weight. Animals were anesthetized and held with the dorsal end facing down. Dosing materials were administered at a rate of ~1 μL/10 seconds split equally through both nostrils. Animal body weights ranged from 35.5 g to 47.2 g (mean of 41.2 g) for the insulin dose group and from 32.5 g to 47.0 g (mean of 38.2 g) for the Sialong dose group.

Clinical signs were recorded twice daily (a.m. and p.m.). Body weights were recorded on the study day 1 and 2 (prior to euthanasia).

3. Biodistribution Blood and Tissue Sampling

At nominal time points post-dose, animals were sacrificed followed by blood collection, perfusion (perfusate contained 2.7% w/v BSA and 100 U/mL heparin in 1×PBS pH7.4), and tissue collection. The olfactory bulbs were included in the collection of the brain tissues. All tissues were stored at nominal −80° C. until assay. Whole tissue samples were collected. Brain was divided into two sections longitudinally. Half was assayed as described below and half was snap-frozen and stored at −80 C for storage. Sample matrices and total number of samples collected in the study for each dose group were stored at nominal −80° C. (Table 8).

TABLE 8

Sample Collection

| Matrix | Vehicle | Insulin$^{AF647}$ | Sialong$^{AF647}$ |
|---|---|---|---|
| Brain-1 | 5 | 40 | 40 |
| Brain-2 | 5 | 40 | 40 |
| Feces | — | 10 | 10 |
| Heart | 5 | 40 | 40 |
| Kidney | 5 | 40 | 40 |
| Liver | 5 | 40 | 40 |
| Lung | 5 | 40 | 40 |
| Plasma | 5 | 40 | 40 |
| Spleen | 5 | 40 | 40 |
| Urine | — | 10 | 10 |

4. Bioanalytical Phase

Brain tissue samples were assayed using acidified ethanol extraction overnight followed by 4 hours of tandem enzyme digest, as described above. The test articles described above were used as calibration standards.

TABLE 9

Determination Insulin and Sialong Levels in Mouse Brain

| Insulin in Brain | | | Sialong in Brain | | |
|---|---|---|---|---|---|
| Expected Conc (ng/g) | Observed Conc (ng/g) | % Bias | Expected Conc (ng/g) | Observed Conc (ng/g) | % Bias |
| 10 | — | — | 157 | — | — |
| 20 | — | — | 300 | 349 | 16.4 |
| 45 | 47.2 | 4.9 | 600 | 510 | −15.0 |
|  | 43.1 | −4.2 |  |  |  |
| 75 | 70.5 | −6.0 | 900 | 954 | 6.0 |
|  | 76.7 | 2.3 |  |  |  |
| 100 | 104 | 4.0 | 2000 | 1990 | −0.4 |
|  | 100 | 0.0 |  |  |  |
| 200 | 193 | −3.5 | 4000 | 4000 | 0.1 |
|  | 206 | 3.0 |  |  |  |
| Regression Method | Quadratic | | 5PL (Marquardt) | | |
| Weighting | $1/X^2$ | | 1/Y | | |
| $R^2$ | 0.9916 | | 0.9987 | | |

As depicted in Table 9, the effective assay LLOQ for insulin was observed at 45 ng/g and the effective assay LLOQ for Sialong was observed at 300 ng/g.

TABLE 10

Insulin and Sialong Concentrations from Brain Test Sample

| Dose Group | Time point | Insulin Conc (ng/g) Individual | Mean | Median | Sialong Conc (ng/g) Individual | Mean | Median | Observations |
|---|---|---|---|---|---|---|---|---|
| Vehicle Control | 10 m | <LLOQ | <LLOQ | <LLOQ | <LLOQ | <LLOQ | <LLOQ | |
| | | <LLOQ | | | <LLOQ | | | |
| | | <LLOQ | | | <LLOQ | | | |
| | | <LLOQ | | | <LLOQ | | | |
| | | <LLOQ | | | <LLOQ | | | |
| Insulin or Sialong | 0 m | <LLOQ | <LLOQ | <LLOQ | <LLOQ | <LLOQ | <LLOQ | |
| | | <LLOQ | | | <LLOQ | | | |
| | | <LLOQ | | | <LLOQ | | | |
| | | <LLOQ | | | <LLOQ | | | |
| | | <LLOQ | | | <LLOQ | | | |
| | 5 m | <LLOQ | <LLOQ | <LLOQ | 526 | 977 (45.9% CV) | 1107 | |
| | | <LLOQ | | | 1107 | | | |
| | | <LLOQ | | | 1502 | | | |
| | | <LLOQ | | | 495 | | | |
| | | 165 | | | 1254 | | | Possible outlier for insulin result |
| | 10 m | <LLOQ | <LLOQ | <LLOQ | 642 | 1142 (63.1% CV) | 797 | |
| | | <LLOQ | | | 1676 | | | |
| | | <LLOQ | | | 2593 | | | |
| | | <LLOQ | | | 797 | | | |
| | | <LLOQ | | | <LLOQ | | | Possible outlier for Sialong result |
| | 30 m | <LLOQ | <LLOQ | <LLOQ | <LLOQ | 346 | <LLOQ | Possible outlier for Sialong result |
| | | <LLOQ | | | <LLOQ | | | Possible outlier for Sialong result |
| | | | | | 903 | | | |
| | | <LLOQ | | | 826 | | | |
| | 1 h | <LLOQ | <LLOQ | <LLOQ | <LLOQ | <LLOQ | <LLOQ | |
| | | <LLOQ | | | <LLOQ | | | |
| | | <LLOQ | | | <LLOQ | | | |
| | | <LLOQ | | | <LLOQ | | | |
| | | <LLOQ | | | 942 | | | Possible outlier for Sialong result |
| | 2 h | <LLOQ | <LLOQ | <LLOQ | 589 | <LLOQ | <LLOQ | Possible outlier for Sialong result |
| | | <LLOQ | | | <LLOQ | | | |
| | | <LLOQ | | | <LLOQ | | | |
| | | <LLOQ | | | <LLOQ | | | |
| | | <LLOQ | | | <LLOQ | | | |
| | 4 h | <LLOQ | <LLOQ | <LLOQ | <LLOQ | <LLOQ | <LLOQ | |
| | | <LLOQ | | | <LLOQ | | | |
| | | <LLOQ | | | <LLOQ | | | |
| | | <LLOQ | | | <LLOQ | | | |
| | | <LLOQ | | | <LLOQ | | | |
| | 8 h | <LLOQ | <LLOQ | <LLOQ | <LLOQ | <LLOQ | <LLOQ | |
| | | <LLOQ | | | 954 | | | Possible outlier for Sialong result |
| | | <LLOQ | | | <LLOQ | | | |
| | | <LLOQ | | | <LLOQ | | | |
| | | <LLOQ | | | <LLOQ | | | |

TABLE 11

Insulin and Sialong Concentrations from Brain Test Sample

| | | Insulin Group | | | | | Sialong Group | | | | |
|---|---|---|---|---|---|---|---|---|---|---|---|
| Time point | Animal No. | Body Wt. (g) | Actual Dosed (μg) | Total Brain Wt. (mg) | Ind. Insulin Conc. (ng/g) | % Dose | Animal No. | Body Wt. (g) | Actual Dosed (μg) | Total Brain Wt. (mg) | Ind. Sialong Conc. (ng/g) | % Dose |
| Vehicle Control (10 m) | 1 | 39.4 | 0 | 596.0 | <LLOQ | — | 1 | 39.4 | 0 | 596.0 | <LLOQ | — |
| | 2 | 36.0 | 0 | 543.0 | <LLOQ | — | 2 | 36.0 | 0 | 543.0 | <LLOQ | — |
| | 3 | 35.6 | 0 | 472.0 | <LLOQ | — | 3 | 35.6 | 0 | 472.0 | <LLOQ | — |
| | 4 | 39.4 | 0 | 535.0 | <LLOQ | — | 4 | 39.4 | 0 | 535.0 | <LLOQ | — |
| | 5 | 41.8 | 0 | 574.0 | <LLOQ | — | 5 | 41.8 | 0 | 574.0 | <LLOQ | — |

TABLE 11-continued

Insulin and Sialong Concentrations from Brain Test Sample

| | Insulin Group | | | | | Sialong Group | | | | |
|---|---|---|---|---|---|---|---|---|---|---|
| Time point | Animal No. | Body Wt. (g) | Actual Dosed (μg) | Total Brain Wt. (mg) | Ind. Insulin Conc. (ng/g) | % Dose | Animal No. | Body Wt. (g) | Actual Dosed (μg) | Total Brain Wt. (mg) | Ind. Sialong Conc. (ng/g) | % Dose |

| Time point | Animal No. | Body Wt. (g) | Actual Dosed (μg) | Total Brain Wt. (mg) | Ind. Insulin Conc. (ng/g) | % Dose | Animal No. | Body Wt. (g) | Actual Dosed (μg) | Total Brain Wt. (mg) | Ind. Sialong Conc. (ng/g) | % Dose |
|---|---|---|---|---|---|---|---|---|---|---|---|---|
| 0 m | 51 | 41.9 | — | 581.9 | <LLOQ | — | 6 | 42.4 | — | 537.7 | <LLOQ | — |
| | 52 | 42.0 | — | 551.3 | <LLOQ | — | 7 | 42.7 | — | 526.6 | <LLOQ | — |
| | 53 | 39.8 | — | 529.9 | <LLOQ | — | 8 | 38.0 | — | 494.6 | <LLOQ | — |
| | 54 | 42.2 | — | 528.2 | <LLOQ | — | 9 | 41.4 | — | 521.4 | <LLOQ | — |
| | 55 | 39.4 | — | 517.4 | <LLOQ | — | 10 | 38.9 | — | 527.2 | <LLOQ | — |
| 5 m | 56 | 41.7 | 37.5 | 520.0 | <LLOQ | — | 11 | 47.0 | 148 | 566.4 | 526 | 0.20 |
| | 57 | 40.0 | 36.0 | 523.4 | <LLOQ | — | 12 | 38.4 | 121 | 547.8 | 1107 | 0.50 |
| | 58 | 41.7 | 37.5 | 505.0 | <LLOQ | — | 13 | 35.0 | 110 | 540.7 | 1502 | 0.74 |
| | 59 | 41.2 | 37.1 | 543.0 | <LLOQ | — | 14 | 39.2 | 123 | 553.8 | 495 | 0.22 |
| | 60 | 42.0 | 37.8 | 533.5 | 165 | 0.23 | 15 | 44.9 | 141 | 531.1 | 1254 | 0.47 |
| 10 m | 61 | 42.2 | 38.0 | 574.8 | <LLOQ | — | 16 | 42.5 | 134 | 558.6 | 642 | 0.27 |
| | 62 | 40.8 | 36.7 | 577.4 | <LLOQ | — | 17 | 33.4 | 105 | 473.4 | 1676 | 0.76 |
| | 63 | 40.3 | 36.3 | 561.9 | <LLOQ | — | 18 | 39.2 | 123 | 601.9 | 2593 | 1.27 |
| | 64 | 40.5 | 36.5 | 536.7 | <LLOQ | — | 19 | 37.1 | 117 | 534.5 | 797 | 0.36 |
| | 65 | 44.5 | 40.1 | 441.0 | <LLOQ | — | 20 | 38.3 | 121 | 522.7 | <LLOQ | — |
| 30 m | 66 | 41.6 | 37.4 | 526.7 | <LLOQ | — | 21 | 41.5 | 131 | 580.1 | <LLOQ | — |
| | 67 | 39.4 | 35.5 | 519.6 | <LLOQ | — | 22 | 32.5 | 102 | 531.9 | <LLOQ | — |
| | 68 | 42.3 | 38.1 | 519.1 | <LLOQ | — | 23 | 42.0 | 132 | 534.7 | 903 | 0.37 |
| | 69 | 43.7 | 39.3 | 514.9 | <LLOQ | — | 24 | 43.7 | 138 | 509.1 | <LLOQ | — |
| | 70 | 47.2 | 42.5 | 590.3 | <LLOQ | — | 25 | 37.2 | 117 | 506.3 | 826 | 0.36 |
| 1 h | 71 | 39.7 | 35.7 | 558.4 | <LLOQ | — | 26 | 40.5 | 128 | 504.2 | <LLOQ | — |
| | 72 | 38.4 | 34.6 | 509.7 | <LLOQ | — | 27 | 36.5 | 115 | 493.2 | <LLOQ | — |
| | 73 | 42.1 | 37.9 | 527.9 | <LLOQ | — | 28 | 41.6 | 131 | 542.7 | <LLOQ | — |
| | 74 | 41.2 | 37.1 | 498.7 | <LLOQ | — | 29 | 39.4 | 124 | 551.8 | <LLOQ | — |
| | 75 | 38.5 | 34.7 | 514.4 | <LLOQ | — | 30 | 37.7 | 119 | 534.5 | 942 | 0.42 |
| 2 h | 76 | 45.1 | 40.6 | 554.1 | <LLOQ | — | 31 | 39.4 | 124 | 602.1 | 589 | 0.29 |
| | 77 | 42.0 | 37.8 | 508.0 | <LLOQ | — | 32 | 36.3 | 114 | 492.2 | <LLOQ | — |
| | 78 | 38.2 | 34.4 | 517.8 | <LLOQ | — | 33 | 36.8 | 116 | 505.5 | <LLOQ | — |
| | 79 | 40.7 | 36.6 | 547.2 | <LLOQ | — | 34 | 39.4 | 124 | 522.6 | <LLOQ | — |
| | 80 | 41.8 | 37.6 | 543.5 | <LLOQ | — | 35 | 35.5 | 112 | 528.2 | <LLOQ | — |
| 4 h | 81 | 41.1 | 37.0 | 518.9 | <LLOQ | — | 36 | 38.2 | 120 | 488.3 | <LLOQ | — |
| | 82 | 43.0 | 38.7 | 515.8 | <LLOQ | — | 37 | 40.2 | 127 | 540.0 | <LLOQ | — |
| | 83 | 41.9 | 37.7 | 502.2 | <LLOQ | — | 38 | 37.5 | 118 | 535.2 | <LLOQ | — |
| | 84 | 41.9 | 37.7 | 526.7 | <LLOQ | — | 39 | 37.4 | 118 | 534.5 | <LLOQ | — |
| | 85 | 35.5 | 32.0 | 520.7 | <LLOQ | — | 40 | 38.3 | 121 | 548.9 | <LLOQ | — |
| 8 h | 86 | 39.3 | 35.4 | 549.8 | <LLOQ | — | 41 | 35.5 | 112 | 485.6 | <LLOQ | — |
| | 87 | 43.1 | 38.8 | 482.2 | <LLOQ | — | 42 | 37.0 | 117 | 491.0 | 954 | 0.40 |
| | 88 | 42.9 | 38.6 | 539.6 | <LLOQ | — | 43 | 33.0 | 104 | 480.0 | <LLOQ | — |
| | 89 | 40.8 | 36.7 | 507.1 | <LLOQ | — | 44 | 34.8 | 110 | 492.4 | <LLOQ | — |
| | 90 | 43.1 | 38.8 | 515.6 | <LLOQ | — | 45 | 33.2 | 105 | 524.2 | <LLOQ | — |

TABLE 12

Brain Weights

| Time point | Animal No. | Brain-1 Wt (mg) | Brain-2 Wt (mg) | Total Brain Wt (mg) | Animal | Brain-1 Wt (mg) | Brain-2 Wt (mg) | Total Brain Wt (mg) |
|---|---|---|---|---|---|---|---|---|
| Vehicle Control (1o m) | 001 | 279.0 | 317.0 | 596.0 | | | | |
| | 002 | 263.0 | 280.0 | 543.0 | | | | |
| | 003 | 214.0 | 258.0 | 472.0 | | | | |
| | 004 | 250.0 | 285.0 | 535.0 | | | | |
| | 005 | 291.0 | 283.0 | 574.0 | | | | |
| 0 m | 006 | 259.2 | 278.5 | 537.7 | 051 | 304.4 | 277.5 | 581.9 |
| | 007 | 282.9 | 243.7 | 526.6 | 052 | 262 | 289.3 | 551.3 |
| | 008 | 229.2 | 265.4 | 494.6 | 053 | 266.2 | 263.7 | 529.9 |
| | 009 | 275.9 | 245.5 | 521.4 | 054 | 265 | 263.2 | 528.2 |
| | 010 | 274.7 | 252.5 | 527.2 | 055 | 252.3 | 265.1 | 517.4 |
| 5 m | 011 | 295.1 | 271.3 | 566.4 | 056 | 307.2 | 212.8 | 520 |
| | 012 | 256.5 | 291.3 | 547.8 | 057 | 280 | 243.4 | 523.4 |
| | 013 | 245.5 | 295.2 | 540.7 | 058 | 266.4 | 238.6 | 505 |
| | 014 | 282.6 | 271.2 | 553.8 | 059 | 275.4 | 267.6 | 543 |
| | 015 | 267.6 | 263.5 | 531.1 | 060 | 283.8 | 249.7 | 533.5 |

TABLE 12-continued

Brain Weights

| Time point | Animal No. | Brain-1 Wt (mg) | Brain-2 Wt (mg) | Total Brain Wt (mg) | Animal | Brain-1 Wt (mg) | Brain-2 Wt (mg) | Total Brain Wt (mg) |
|---|---|---|---|---|---|---|---|---|
| 10 m | 016 | 263.1 | 295.5 | 558.6 | 061 | 305.2 | 269.6 | 574.8 |
|  | 017 | 247.7 | 225.7 | 473.4 | 062 | 269.1 | 308.3 | 577.4 |
|  | 018 | 302.6 | 299.3 | 601.9 | 063 | 251.6 | 310.3 | 561.9 |
|  | 019 | 307.6 | 226.9 | 534.5 | 064 | 288 | 248.7 | 536.7 |
|  | 020 | 245.1 | 277.6 | 522.7 | 065 | 229.5 | 211.5 | 441 |
| 30 m | 021 | 284.9 | 295.2 | 580.1 | 066 | 279.9 | 246.8 | 526.7 |
|  | 022 | 292 | 239.9 | 531.9 | 067 | 252.9 | 266.7 | 519.6 |
|  | 023 | 238.6 | 296.1 | 534.7 | 068 | 272.3 | 246.8 | 519.1 |
|  | 024 | 253.1 | 256 | 509.1 | 069 | 231.4 | 283.5 | 514.9 |
|  | 025 | 268.7 | 237.6 | 506.3 | 070 | 354 | 236.3 | 590.3 |
| 1 h | 026 | 282.1 | 222.1 | 504.2 | 071 | 310.5 | 247.9 | 558.4 |
|  | 027 | 222.2 | 271 | 493.2 | 072 | 277.5 | 232.2 | 509.7 |
|  | 028 | 308.8 | 233.9 | 542.7 | 073 | 296 | 231.9 | 527.9 |
|  | 029 | 276 | 275.8 | 551.8 | 074 | 243.7 | 255 | 498.7 |
|  | 030 | 267.3 | 267.2 | 534.5 | 075 | 280.1 | 234.3 | 514.4 |
| 2 h | 031 | 282.8 | 319.3 | 602.1 | 076 | 269.5 | 284.6 | 554.1 |
|  | 032 | 268.1 | 224.1 | 492.2 | 077 | 268.4 | 239.6 | 508 |
|  | 033 | 271.4 | 234.1 | 505.5 | 078 | 246.9 | 270.9 | 517.8 |
|  | 034 | 262.2 | 260.4 | 522.6 | 079 | 291.3 | 255.9 | 547.2 |
|  | 035 | 316 | 212.2 | 528.2 | 080 | 266.3 | 277.2 | 543.5 |
| 4 h | 036 | 264.8 | 223.5 | 488.3 | 081 | 249.5 | 269.4 | 518.9 |
|  | 037 | 248.1 | 291.9 | 540 | 082 | 282.4 | 233.4 | 515.8 |
|  | 038 | 292 | 243.2 | 535.2 | 083 | 235.7 | 266.5 | 502.2 |
|  | 039 | 241.5 | 293 | 534.5 | 084 | 283.4 | 243.3 | 526.7 |
|  | 040 | 293.3 | 255.6 | 548.9 | 085 | 256.6 | 264.1 | 520.7 |
| 8 h | 041 | 244.4 | 241.2 | 485.6 | 086 | 289.2 | 260.6 | 549.8 |
|  | 042 | 247.5 | 243.5 | 491 | 087 | 251.2 | 231 | 482.2 |
|  | 043 | 252.5 | 227.5 | 480 | 088 | 273.5 | 266.1 | 539.6 |
|  | 044 | 249.3 | 243.1 | 492.4 | 089 | 238 | 269.1 | 507.1 |
|  | 045 | 282.4 | 241.8 | 524.2 | 090 | 273.9 | 241.7 | 515.6 |

As depicted in Tables 10 and 11, insulin levels were below LLOQ for all time points evaluated except for one animal (animal ID 060) at the 5-minute time point. Because all other samples showed <LLOQ results, the raw fluorescence responses (animal 060 excluded) between vehicle control group and insulin dose group were compared by a one-way ANOVA test to determine whether there is any significant difference between fluorescence signal among the different time points. Statistical analysis revealed that there were no significant differences (p>0.1) between all of the time points evaluated.

As depicted in Table 11, Sialong was detected at 5 minutes post-administration and peaked at 10 minutes reaching mean concentration levels of 1142 ng/g in the brain and was observed at 30 minutes. Levels of Sialong detected were highly variable between animals; however, no assay anomalies were noted during the preparation of this assay batch. As well, Sialong was observed in several animals after 30 minutes those may potentially be outliers.

In general, insulin was not appreciably distributed to the brain at any of the time points evaluated, whereas Sialong was detected 5 minutes post-dose, peaked at 10 minutes at levels of 1142 ng/g, and decreased rapidly to near LLOQ levels by 30 minutes.

The assay performances for both insulin and Sialong brain assays were within acceptance criteria. For both assays, duplicate calibration curves were prepared in the same brain matrices as study test samples and extracted alongside (bracketing) test samples using identical procedures. No drifting of fluorescent signal was observed and no outlying values were observed from these standards, indicating that the observations of some of the outlying test sample results were likely not from extraction and assay, but from the samples themselves.

During sample collection, two brain halves were collected by cutting the brain longitudinally. One half was fully homogenized and an aliquot was taken for extraction. Remaining homogenate was returned to storage. The second half was stored frozen as intact brain tissue samples. Both the homogenate and second brain half should be analyzed in parallel hopefully to generate data useful for further interpretation of the outlying results; whether it may be a homogenization contamination, dosing variability due to "sneezing" by irritation, or real biological phenomenon.

Figure 5:
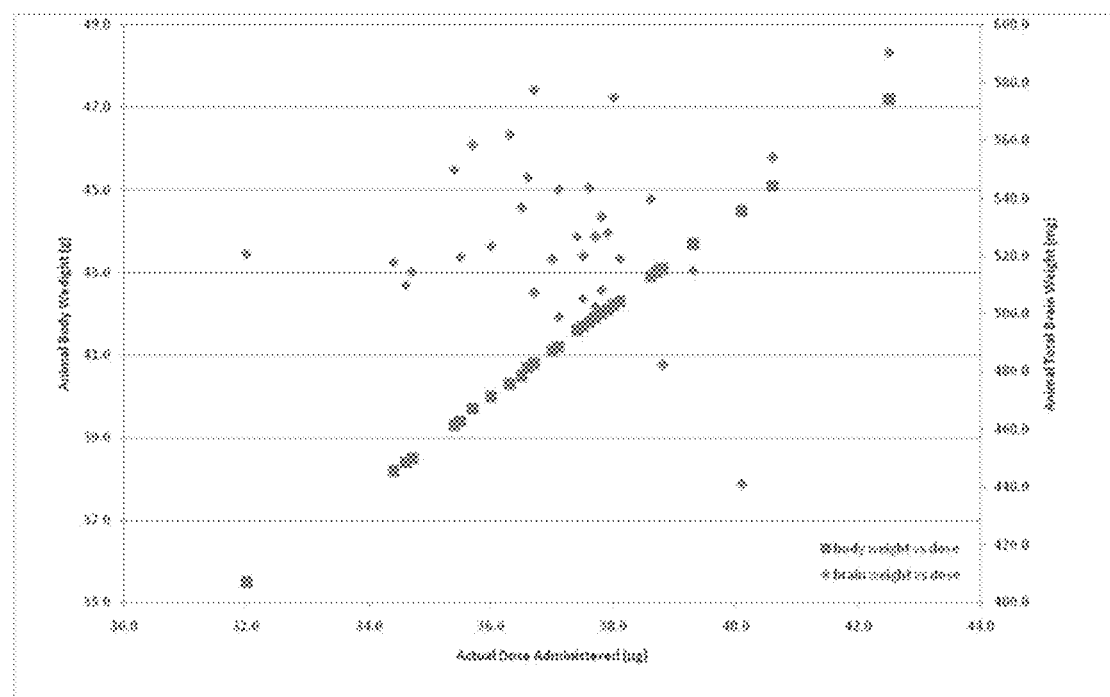
FIG. 5 is a correlation plot between the actual Sialong dose administered versus the mouse body and total brain weights recorded during the study.

FIG. 5 is a correlation plot between the actual dose administered versus the mouse body and total brain weights recorded during the study. As expected, dose vs body weight correlate very well. However, there did not appear to be any correlation between dose vs brain weight. This observation could explain some of the variability between Sialong results observed at the 5 and 10 minutes time points.

These data demonstrate that a COA-insulin conjugate of the present invention can be used to deliver insulin to the brain through the nasal mucosa, and suggest that COA may be an enhancing agent which facilitates the transport of therapeutic agents through various mucosa barriers.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of administering a therapeutically effective amount of an insulin to the brain of an individual, the method comprising intranasal administration of a pharmaceutical composition comprising a population of the insulin and/or an insulin-like protein attached to a polysialic acid where administration results in a therapeutically effective amount in the brain but not the serum of the individual.

2. The method according to claim 1, wherein the insulin is a natural insulin derived from an animal.

3. The method according to claim 2, wherein the natural insulin is derived from a human.

4. The method according to claim 1, wherein the insulin comprised SEQ ID NO: 1, SEQ ID NO: 2, or SEQ ID NO: 3.

5. The method according to claim 1, wherein the insulin-like protein comprises the A-chain/B-chain amino acid sequence combinations of SEQ ID NO: 3/SEQ ID NO: 4, or SEQ ID NO: 3/SEQ ID NO: 5, or SEQ ID NO: 3/SEQ ID NO: 6, or SEQ ID NO: 3/SEQ ID NO: 7, or SEQ ID NO: 3/SEQ ID NO: 8.

6. The method according to claim 1, wherein the polysialic acid is a homopolymeric form, or a heteropolymeric form.

7. The method according to claim 6, wherein the homopolymeric form includes an alternating alpha-2,8 linked polysialic acid.

8. The method according to claim 7, wherein the polysialic acid comprises about 40 to about 150 sialic acid units.

9. The method according to claim 6, wherein the heteropolymeric form includes an alternating alpha-2,8 alpha-2,9 linked polysialic acid.

10. The method according to claim 1, wherein the polysialic acid comprises about 2 to about 200 sialic acid units.

11. The method according to claim 10, wherein the polysialic acid comprises about 20 to about 175 sialic acid units.

12. The method according to claim 1, wherein the polysialic acid has an average molecular weight in the range of about 2 kDa to about 100 kDa.

13. The method according to claim 12, wherein the polysialic acid has an average molecular weight in the range of about 5 kDa to about 80 kDa.

14. The method according to claim 1, wherein the polysialic acid is attached to the protein by its reducing end terminal unit, its non-reducing terminal unit, or both.

15. The method according to claim 1, wherein the population of the insulin and/or an insulin-like protein attached to the polysialic acid has a polydispersity of about 1.05 to about 1.3.

16. The method according to claim 15, wherein the population of the insulin attached to the polysialic acid has a polydispersity of about 1.05 to about 1.2.

17. The method according to claim 1, wherein the insulin proteins having the polysialic acid attached to the N-terminus of the insulin protein is at least 70% of the total proteins of the population.

18. The method according to claim 1, wherein the insulin proteins having the polysialic acid attached to the N-terminus of the insulin protein is about 80% to about 100% of the total proteins of the population.

19. The method according to claim 1, wherein the population of the insulin and/or an insulin-like protein attached with a polysialic acid is administered to an individual at a dose of between about 0.6 mg/kg to about 3.0 mg/kg.

* * * * *

SEQUENCE LISTING

<160> NUMBER OF SEQ ID NOS: 8

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

```
Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Homo sapiens

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 4
<211> LENGTH: 30
<212> TYPE: PRT
<213> ORGANISM: homo sapiens

<400> SEQUENCE: 4

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30

<210> SEQ ID NO 5
<211> LENGTH: 30
<212> TYPE: PRT
<213> ORGANISM: homo sapiens

<400> SEQUENCE: 5

Phe Val Lys Gln His Leu Cys Gly Ser His Leu Val Glu Ala Leu Tyr
1               5                   10                  15

Leu Val Cys Gly Glu Arg Gly Phe Phe Tyr Thr Ile Lys Thr
            20                  25                  30

<210> SEQ ID NO 6
<211> LENGTH: 30
<212> TYPE: PRT
<213> ORGANISM: homo sapiens

<400> SEQUENCE: 6
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25              30

<210> SEQ ID NO 7
<211> LENGTH: 30
<212> TYPE: PRT
<213> ORGANISM: homo sapiens

<400> SEQUENCE: 7

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Pro Lys Thr
            20                  25              30

<210> SEQ ID NO 8
<211> LENGTH: 30
<212> TYPE: PRT
<213> ORGANISM: Homo sapiens

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25              30
```